United States Patent [19]
Sheldon et al.

[11] Patent Number: 6,044,297
[45] Date of Patent: Mar. 28, 2000

[54] POSTURE AND DEVICE ORIENTATION AND CALIBRATION FOR IMPLANTABLE MEDICAL DEVICES

[75] Inventors: Todd J. Sheldon, North Oaks; William J. Combs, Eden Prarie; Mark K. Erickson, Brooklyn Park; Can Cinbis, Shoreview, all of Minn.

[73] Assignee: Medtronic, Inc., Minneapolis, Minn.

[21] Appl. No.: 09/160,647

[22] Filed: Sep. 25, 1998

[51] Int. Cl.$^7$ .................................................. A61N 1/362
[52] U.S. Cl. ............................................ 607/17; 600/585
[58] Field of Search ........................ 607/17–19; 600/587, 600/595

[56] References Cited

U.S. PATENT DOCUMENTS

| | | |
|---|---|---|
| 4,257,423 | 3/1981 | McDonald et al. |
| 4,374,382 | 2/1983 | Markowitz . |
| 4,428,378 | 1/1984 | Anderson et al. |
| 4,556,063 | 12/1985 | Thompson et al. |
| 4,846,195 | 7/1989 | Alt . |
| 4,869,251 | 9/1989 | Lekholm et al. |
| 5,010,893 | 4/1991 | Sholder et al. |
| 5,031,618 | 7/1991 | Mullett . |
| 5,233,984 | 8/1993 | Thompson . |
| 5,342,404 | 8/1994 | Alt et al. |
| 5,345,824 | 9/1994 | Sherman et al. |
| 5,354,317 | 10/1994 | Alt . |
| 5,593,431 | 1/1997 | Sheldon . |
| 5,725,562 | 3/1998 | Sheldon . |
| 5,780,742 | 7/1998 | Burs et al. |

OTHER PUBLICATIONS

PACE vol. 11 pp.–1875–1881 Nov. 1988 Part ii Entitled: A New Mechanical Sensor for detecting Body Activity and Posture.

WLWCTRONIC Design Aug. 8, 1991 Entitled: Airbags Boom WIHEN IC Accelerometer SEES 50G.

*Primary Examiner*—William E. Kamm
*Assistant Examiner*—George R. Evanisko
*Attorney, Agent, or Firm*—Harold R. Patton; Reed A. Duthler

[57] ABSTRACT

A method of and apparatus for determining the physical posture of a patient's body, having a superior-inferior body axis, an anterior-posterior body axis and a lateral-medial body axis, in relation to earth's gravitational field. A medical device having first, second and, optionally, third accelerometers having sensitive axes mounted orthogonally within an implantable housing is adapted to be implanted with the sensitive axes nominally aligned with ideal X, Y and Z device axes correlated to patient body axes. Each accelerometer generates DC accelerometer signals having characteristic magnitudes and polarities on alignment of the sensitive axis with, against or normal to earth's gravitational field and DC accelerometer signals of varying magnitudes and polarities when not so aligned. The actual pitch and roll angles of the sensitive axes of the accelerometers in the implanted IMD with respect to the true gravitational axes are determined and the yaw angles are determined or estimated. Corrected DC accelerometer output signals are derived from the pitch, roll and yaw angles and are compared to a set of stored thresholds for each body posture to determine the actual body posture. Storage of these comparisons or the raw signals themselves can be used for histogram data to provide theraputic or research benefits also described.

68 Claims, 10 Drawing Sheets

POSTURE AND DEVICE ORIENTATION AND CALIBRATION FOR IMPLANTABLE MEDICAL DEVICES

FIELD OF THE INVENTION

This invention relates to sensing orientation with respect to gravity and with respect to patient posture for implantable medical devices. In its most presently preferred form, the present invention relates to the use of an array of accelerometers that may be three, orthogonally sensitive DC accelerometers for detection of patient posture and activity level for medical monitoring and/or the delivery of device assisted therapies, such as cardiac pacing, drug delivery and the like, by an implantable medical device (IMD), and particularly to the calibration of the accelerometers to account for actual implantation orientation.

DESCRIPTION OF THE PRIOR ART

Commonly assigned U.S. Pat. Nos. 5,593,431 and 5,725,562, both incorporated herein by reference, set forth IMD systems for determining the physical posture of a patient's body, having a superior-inferior (S-I) body axis, an anterior-posterior (A-P) body axis and a lateral-medial (L-M) body axis, in relation to gravitational force imposed by earth's gravitational field. In certain embodiments, the IMDs disclosed therein have first, second and third DC accelerometers having sensitive axes mounted orthogonally within an IMD housing is adapted to be implanted with the sensitive axes generally aligned with the patient s body axes. Each DC accelerometer generates DC accelerometer signals having characteristic magnitudes and polarities on alignment of the sensitive axis with, against or normal to earth's gravitational field and DC accelerometer signals of varying magnitudes and polarities when not so aligned. Body position can be determined through comparison of the magnitudes and polarities of the DC accelerometer signals with the characteristic magnitudes and polarities. A patient activity signal may also be determined from the frequency of body movements recurring over a time unit effecting magnitude changes in the DC accelerometer signals within a certain range of magnitude and frequency. The activity and body position signals may be stored in a monitoring mode and/or used to effect the delivery of a therapy to the patient, e.g. by controlling the pacing rate of a rate responsive pacemaker or delivery of a drug or tachyarrhythmia therapy.

AC accelerometers may be used but are not preferred since they do not produce a signal directly relatable to gravity orientation.

Rate responsive pacing has been widely adopted for adjusting pacing rate to the physiologic needs of the patient in relatively recent years. The introduction of the Medtronic® Activitrax® pacemaker, embodying the invention of commonly assigned U.S. Pat. No. 4,428,378, provided patients with a pacing rate responsive capability dependent on the level of patient activity. A piezoelectric crystal bonded to the interior of the implantable pulse generator can or case is employed in that pacemaker and successor models to provide a pulse output signal related to the pressure wave generated by a patient's footfall and conducted through the body to the crystal. Thus, low frequency activity signals recurring at the patient's rate of walking or running could be sensed and processed to derive a pacing rate appropriate to the level of activity.

Activity sensor configurations employing integrated circuit, AC accelerometers on an IC chip inside the pacemaker are also being employed in the EXCEL VR pacemaker sold by Cardiac Pacemakers, Inc., and in similar rate responsive pacemakers sold by other manufacturers. The AC accelerometer is formed of a silicon beam mass suspended on the IC that swings or moves in response to shock waves caused by body motion and provides an output signal having a magnitude dependent on the rate of movement.

Like the piezoelectric crystal sensor, there is no signal output from the AC accelerometer in the absence of body motion and related to body position or attitude. In other words, when a patient is at rest, neither activity sensor provides any indication as to whether the patient is upright and awake and resting or lying down and presumably sleeping or resting. A lower sleep pacing rate than the rest pacing rate while awake and upright may be desirable for a given patient. Other sensors for sensing physiologic parameters induced by high levels of exercise have been proposed to detect the physiologic changes accompanying exercise, rest and sleep to trigger appropriate rates. Particularly, to lower the pacing rate during sleep, the inclusion of a real time clock to establish a Circadian rhythm pacing rate have also been proposed. None of these proposed sensors or systems are capable of determining a patient's position or posture.

A mechanical sensor has been proposed in the article "A New Mechanical Sensor for Detecting Body Activity and Posture, Suitable for Rate Responsive Pacing" by Alt et al. (PACE, Vol. 11, pp. 1875–81, November, 1988, Part II) and in U.S. Pat. No. 4,846,195 that involves use of a multi-contact, tilt switch. This switch employs a mercury ball within a container that is proposed to be fixed in the pulse generator case, so that if the pulse generator is implanted at a certain orientation, and stays in that orientation, certain contacts are closed by the mercury ball when the patient is upright and others are closed or none are closed when the patient is prostrate, i.e., either prone or supine. During movement of the body, the mercury ball is expected to jiggle randomly and the number of contacts made per unit of time may be used as a measure of the level of activity. Similar sensors have been proposed in U.S. Pat. Nos. 4,869,251, 5,010,893, 5,031,618 and 5,233,984, incorporated herein by reference.

In the commonly assigned '984 patent, a cubic shaped multi-axis position and activity sensor is employed in rate responsive pacing applications and in the detection of tachycardia based on the patient being supine and inactive. In the commonly assigned '618 patent, a single axis position sensor is employed that is employed to control the therapy delivered by a spinal cord stimulator. The sensors in both patents employ conductive liquids, including an electrolyte or elemental mercury.

The use of a solid state position sensor in the form of a DC accelerometer is proposed in U.S. Pat. Nos. 5,354,317 and 5,342,404, both incorporated herein by reference. The DC accelerometer in a preferred form as in these (and hereby incorporated in it's entireyt by this reference hereinto) and 404 patents, is fabricated in hybrid semiconductor IC form as a polycrystalline silicon, square plate, suspended at its four corners above a well in a single silicon crystal substrate, and associated low pass filter circuits are formed on the same substrate. The suspended plate structure moves between stationary positions with respect to the well on the suspension arms in response to gravitational force, depending on its orientation to the gravitational field. The plate also vibrates on the suspension arms similar to the AC accelerometer in response to acceleration movements of the patient's body.

Any type of accelerometer that can give a DC output that changes with its orientation or position sensitive to the earth's gravity would be useable. An example of a specific accelerometer type can be found in U.S. Pat. No. 5,345,824, assigned to Analog Devices, showing how a sensor with differential capacitive structure provides a signal output based on sensor orientation. Such a signal can be used to provide the DC signal useful for this invention.

In the pacing algorithms disclosed in the '317 patent, different base pacing rates are established depending on the static output of the position sensor that indicate the position of the patient, namely the upright, supine and prone positions, and separate base pacing rates can be set. Rate changes from the base pacing rates dependent on the exercise level of the patient in each position are suggested. Also, when changes in patient position are detected in the absence of physical exercise, the base pacing rate change is smoothed between the old and new rate to avoid a sudden step change.

The rate responsive pacemaker disclosed in the '317 patent offers some discrimination of patient position, but cannot distinguish among various patient positions where the suspended plate structure is aligned at the same angle to earth's gravitational field. The plane of the movable plate is at a fixed angle, e.g. coplanar, to a plane of the pulse generator case. Once the pulse generator is implanted in a patient, the movable plate plane may be aligned generally in parallel with the gravitational field and not detect the gravitational force (i.e., producing a zero amplitude output signal correlated to 0 g). The output of the so-aligned DC accelerometer would be the same whether a patient is standing, sitting or lying on either side, since the plate plane would remain in the same general parallel relationship to the gravitational field in all three positions. However, the pacing rates appropriate in standing, sitting or lying on a side are different when the patient is still.

In the above-incorporated '431 and '562 patents, the posture of the patient is determined through the use of two or more solid state, DC accelerometers mounted in mutual orthogonal relationship within the IMD housing. The two or more accelerometers develop two or more sets of accelerometer output signals having signal amplitudes and polarities that are dependent on the effect of gravity on the accelerometers. Threshold amplitudes are stored in IMD memory that are related to the posture of the patient while standing, sitting, or prostrate in supine, prone, left side and right side positions. The output signal amplitudes are compared to the stored threshold amplitudes, and the posture of the patient is determined from the closest comparison of the output signal amplitudes to he stored threshold amplitudes.

With three DC accelerometers mounted orthogonally, the patient's body posture at rest may be derived and employed, in a pacing context, to set physiologic resting pacing rates appropriate to the patient in each of the possible positions. The body posture may also be used to augment the diagnosis of a malignant tachyarrhythmia to trigger delivery of a cardioversion/defibrillation therapy and/or to be stored with other EGM and physiologic data related to a cardiac arrhythmia episode.

The orthogonally mounted, DC accelerometers are mounted into an IC chip, or to a hybrid circuit board, or otherwise orthogonally mounted so that the three sensitive axes are aligned with the three device positioning axes of the IMD housing that are designated as the X, Y and Z device positioning axes. In relation to a standing patient, these X, Y and Z device positioning axes correlate to L-M, S-I and A-P body axes, respectively, and the IMD case is preferably so marked for reference. The physician can implant and stabilize the IMD in the patient's thorax region so that the X, Y and Z positioning axes are aligned as closely as possible to the corresponding L-M, S-I, and A-P body axes of the patient's thorax. It is assumed that these body axes are aligned with the force of gravity when the patient is standing upright such that the S-I body axis is generally aligned in parallel with the force of gravity or an ideal Y-axis. Similarly, the A-P body axis and the L-M body axis are assumed to be generally aligned orthogonally to the force of gravity and are arbitrarily designated as the ideal Z-axis and ideal X-axis, respectively. The actual alignment of the device axes with the body axes depends on the selected implantation site, care taken during implantation to optimize the alignment, and the patient's anatomy at the implantation site.

Assuming that these device and body axes are aligned, a distinctive output signal amplitude is developed by each DC accelerometer in each patient posture due to the effect of gravity on the DC accelerometer sensitive axis in that posture. The posture of the patient can be derived from the comparison of the DC accelerometer output signal amplitudes with the stored threshold amplitudes as described above.

However, in practice, the implanted IMD housing is never perfectly aligned so that the sensitive axes of the three DC accelerometers are aligned optimally to the corresponding ideal device axes. Moreover, IMDs frequently migrate or are moved over time from the initial implant position even if the IMD housing is initially implanted in the proper orientation. Consequently, the magnitudes and polarities of the output signals of the three DC accelerometers can change with changed orientation of the IMD housing, rendering accurate determination of posture difficult and leading to miscalculation of posture in extreme cases.

These problems are generally recognized in the above-incorporated '431 and '562 patents, and a work-up routine is described to perform posture detection even though the device axes are not truly aligned with the ideal device axes. This is accomplished in the '431 patent by having the patient assume the standing, sitting, supine, prone, left side and right side resting positions to accumulate average output signals of each of the DC accelerometers in IMD. A programmer is employed to trigger the telemetry out of the accumulated sets of signals for external storage and display. Then, the deviations in the output signal amplitudes from a standard amplitude expected from alignment of the sensitive axis with earth's gravitational field may be derived and employed to normalize the actual output signals.

The normalization can be effected by transmitting correction factors to the IMD to be used to correct the actual accelerometer signal amplitudes or to adjust the threshold amplitudes that they are compared against, which is specifically described in the '431 patent. In the described calibration routine, sets of "posture confidence intervals" are calculated from the actual output signal amplitudes of the accelerometers and stored in the IMD memory as threshold amplitude ranges specific to each body position for comparison with the output signal amplitude of each accelerometer to determine the body position. This is a rather cumbersome procedure that may have to be repeated periodically over the life of the IMD to account for continued migration and reorientation of the device relative to the body.

It is suggested in the above-incorporated '317 patent that the output signal from the single DC accelerometer that is intended to be aligned with the S-I body axis or with the A-P body axis or the L-M body axis is calibrated at implantation to account for deviation of the accelerometer axis from the intended axis. In addition, it is suggested that an autocalibration routine be performed automatically from time to time when the patient is determined to be active. It is assumed that the patient is in an upright or standing stance when a certain level of exercise is detected that is consistent with walking or bicycling, for example.

The above-incorporated '404 patent describes use of two solid state accelerometers oriented at 90° to one another as an alternative to the preferred use of two mercury ball activity sensors aligned in the same manner. The sensors are aligned in the IMD so that the sensitive axis of one of the sensors will be implanted nominally in alignment with the gravitational Y-axis when the patient is in an upright posture. It is also suggested that a calibration routine be performed.

No particular calibration technique is described in either of the above-incorporated '404 or '317 patents. It appears that the sensor output signals are adjusted to account for the tilts in the sensors. In the above-incorporated '404 patent, it appears that the calibration may take place while the patient assumes the upright, supine and prone postures.

In view of the cumbersome procedure for calibrating the three orthogonal DC accelerometers, it would be preferable to simply determine the actual orientations of the X, Y and Z device axes to the corresponding X, Y and Z ideal axes from which highly accurate calibration factors can be determined to correct the actual output signal amplitudes and polarities.

SUMMARY OF THE INVENTION

In view of the above, it is an object of the present invention to provide a multi-axis, solid state position and activity sensor operable along at least two orthogonal sensitive axes calibrated for deviations from alignment to corresponding ideal axes to distinguish the posture or positioning attitude of the patient at rest and at levels of exercise.

It is a further an object of the present invention to employ such a sensor to record body position and activity signal levels derived from the output signals of such a sensor.

It is yet a further an object of the present invention to employ such a sensor to employ body position and activity signal levels derived from the output signals of such a sensor in controlling the delivery of a therapy to a patient.

In a specific context, it is an object of the present invention to provide a calibration routine that is either invoked automatically or in a patient work-up that determines the actual orientations of the sensitive axes of the sensor with respect to ideal axes.

It is yet another object of the present invention to provide a calibration routine in an IMD having such a sensor employing three orthogonally disposed DC accelerometers having three orthogonally disposed sensitive axes that is employed to determine the position of the IMD to the patient's body. In particular, it is an object of the invention to determine deviations of the sensitive axes from ideal X, Y and Z axes to determine the position of the IMD expressed in terms of pitch, roll and yaw angular deviations of the sensitive axes from ideal X, Y and Z axes.

Various other types of accelerometers that could be used with this invention are described by and in the background section of U.S. Pat. No. 5,780,742, hereby also incorporated by this reference. The calibration would have to be modified from what is taught herein as dictated by the choice of accelerometer, of course, but the same uses could be made of the data so derived, indicating deviations of the sensitive axes from the ideal, expressed in pitch, roll and yaw parameters.

These and other objects of the invention are realized in a method of and apparatus for determining the physical posture of a patient's body from corrected accelerometer output signals of three accelerometers having sensitive axes aligned to X, Y and Z device axes of an IMD housing implanted in the patient's body in relation to the X, Y and Z ideal axes, respectively. In the practice of the invention, at least the pitch and roll angles of the device axes from the gravitational axes are derived.

In one embodiment, an autocalibration routine is undertaken periodically using accelerometer DC signal data that is stored in a memory in the IMD while the patient is assumed to be upright and that assumes that the yaw angle is insignificant. This embodiment requires no supervisory physician intervention to occur. (If the number of indeterminate posture detections in a given period of time, a flag can be set to cause supervisory personnel to force a new full calibration as in the patient full work -up in the next mentioned embodiment). This autocalibration routine derives the actual device X-axis, Y-axis, and Z-axis with respect to the ideal X-axis, Y-axis, and Z-axis that is used to correct the accelerometer output signals for use in determining instantaneous or current patient posture. The pitch and roll angles or correction factors derived therefrom are averaged for use in the intervals between autocalibration events. One or more of the DC accelerometers can also be used to derive the level of patient activity from the number of changes in signal levels exceeding a certain threshold occurring in a given sampling time period, as is conventional in use of the piezoelectric and AC accelerometer activity sensors described above. The patient is assumed to be upright when an activity level consistent with walking for a specified time interval is determined from the output signals of the DC accelerometers.

In a further embodiment, a patient work-up is initiated from time to time following implantation wherein the patient assumes two orthogonal body positions, e.g. the upright and supine positions. In the full patient work-up routine, any rotation of the plane of the IMD housing defined by the device X-axis and the device Z-axis with respect to the ideal Y-axis resulting in a yaw angle of rotation is determined and taken into account along with the determination of the pitch and roll angles. In this way, any deviations in pitch, roll and yaw from the ideal alignment of the sensitive axes of the DC accelerometers with the ideal X, Y and Z ideal axes are accounted for. The determined pitch, roll and yaw angles and/or correction factors derived therefrom are maintained in IMD memory for use in correcting the measured DC accelerometer output signals between patient work-ups.

In both cases, the actual orientations of the sensitive axes of the DC accelerometers in the implanted IMD, corresponding to the X, Y and Z device axes, with respect to the ideal X. Y and Z axes are determined. Corrected DC accelerometer output signals are derived therefrom and are compared to a set of stored thresholds for each body posture to determine the actual body posture.

In accordance with the preferred embodiments of the invention, the stored posture and activity levels may be retained in a monitor and/or be employed to control the delivery of a variety of therapies, including pacing, cardioversion/defibrillation, other body stimulation therapies, and drug delivery therapies.

In the context of a pacemaker, the method and apparatus of the invention for pacing a patient's heart at a pacing rate dependent on patient activity and the physical posture of a patient's body, the determination of the actual implanted orientations of the mutually orthogonal DC accelerometers and their calibration to account for pitch, roll and yaw angles from the orthogonal ideal X, Y and Z axes in a computationally efficient manner increases the confidence of accuracy of the determination of patient posture. The autocalibration of the three orthogonal DC accelerometers utilizing accelerometer signals which have been stored in memory at a certain exercise level(s) when the patient is assumed to be standing upright overcomes the limitations of calibrating a single DC accelerometer. The incorporation of DC accelerometers in the IMD does not involve acceptance of unusual materials and technology. The calibrated mutually orthogonal DC accelerometers and associated circuits can most usefully be incorporated into a pacemaker pulse generator or other medical device.

By maintaining records of the posture of the patient and the deviation from ideal axes of the IMD's relative orientation to the ideal axes, the data in such records can be used to indicate orientation of a subcutaneous electrode array on the housing of an IMD which also has these accelerometers, to enhance electrogram records however they may be stored. The posture indicated can be used to enhance the rate responsiveness of pacemakers, for example switching from a pacing rate of 50 when a patient is sitting to a rate of 70 upon a clear indication of the patient moving to a standing position. Medical personal may better deal with patients with Orthostatic Hypotension from a record of the amount of time in standing, sitting, and supine positions, relative to significant events such as fainting or feeling faint, which an IMD having the invention can easily store. An IMD can provide rapid atrial and/or dual chamber pacing based on knowledge of when the patient is in an or relatively upright posture. Studies have shown increased pacing rates to be of benefit to some patients with severe postural hypotension, so there is a ready use for this type of posturally enhanced IMD. A physician can adapt therapy for such a patient based on such information. When combined with an indicator of sleep cycle, contemporaneous signals indicating that as patient sat up in bed may indicate a progression of heart failure as patients adapt to their lungs filling with fluid by sitting up during sleep. Together with monitoring heart rate drop, more effective support pacing (at high rates, for example) therapy for Vasovagal Syncope (VVS) can be supplied by a pacemaker that notices that a patient stood up contemporaneously with a rapid drop in heart rate. In addition, pacing therapies for vasovagal syncope, which sense sudden drops in heart rate could use body position as an additional input and withhold therapy when the patient in lying down or in a prostrate position. Symptomatic vasovagal syncope is rare during horizontal body positions but sudden heart rate drops are common during sleep leading to potentially numerous false positive indications and unneeded support pacing, drug or other therapy delivery. Therapies for sleep apnea may be created using posture information, and even patient compliance with exercise programs can be monitored using this information. Numerous other applications for these signals can be thought of and their use in research into the progression of heart disease is only one area.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

The present invention is preferably implemented in any IMD and finds particular utility in the control of pacing rate to account for the level of patient activity and for patient posture and to discriminate between ascending and descending stairs as set forth in the specific embodiments of the above-incorporated '431 and '562 patents. It will also be understood that the present invention may be implemented in implantable tachyarrhythmia control pacemakers, cardioverters, defibrillators and the like. Specifically, the enhanced capability of determining body position may be employed to augment detection of life threatening cardiac arrhythmias that render a patient prostrate. Determination that a patient is upright and active vs. prostrate may be useful in distinguishing a malignant tachyarrythmia from an appropriate or sinus tachycardia.

Furthermore, the present invention may be employed in sleep disorder or apnea monitors to record the body position during episodes. Similarly, the body position may be used to verify that a patient is lying down and likely asleep during an assumed sleep period of a circadian rhythm monitor or to augment a circadian rhythm algorithm for a treatment device. The present invention may also find utility in providing patient position data correlated to the EGM and blood pressure in implantable cardiac EGM and hemodynamic monitors.

Figure 1:
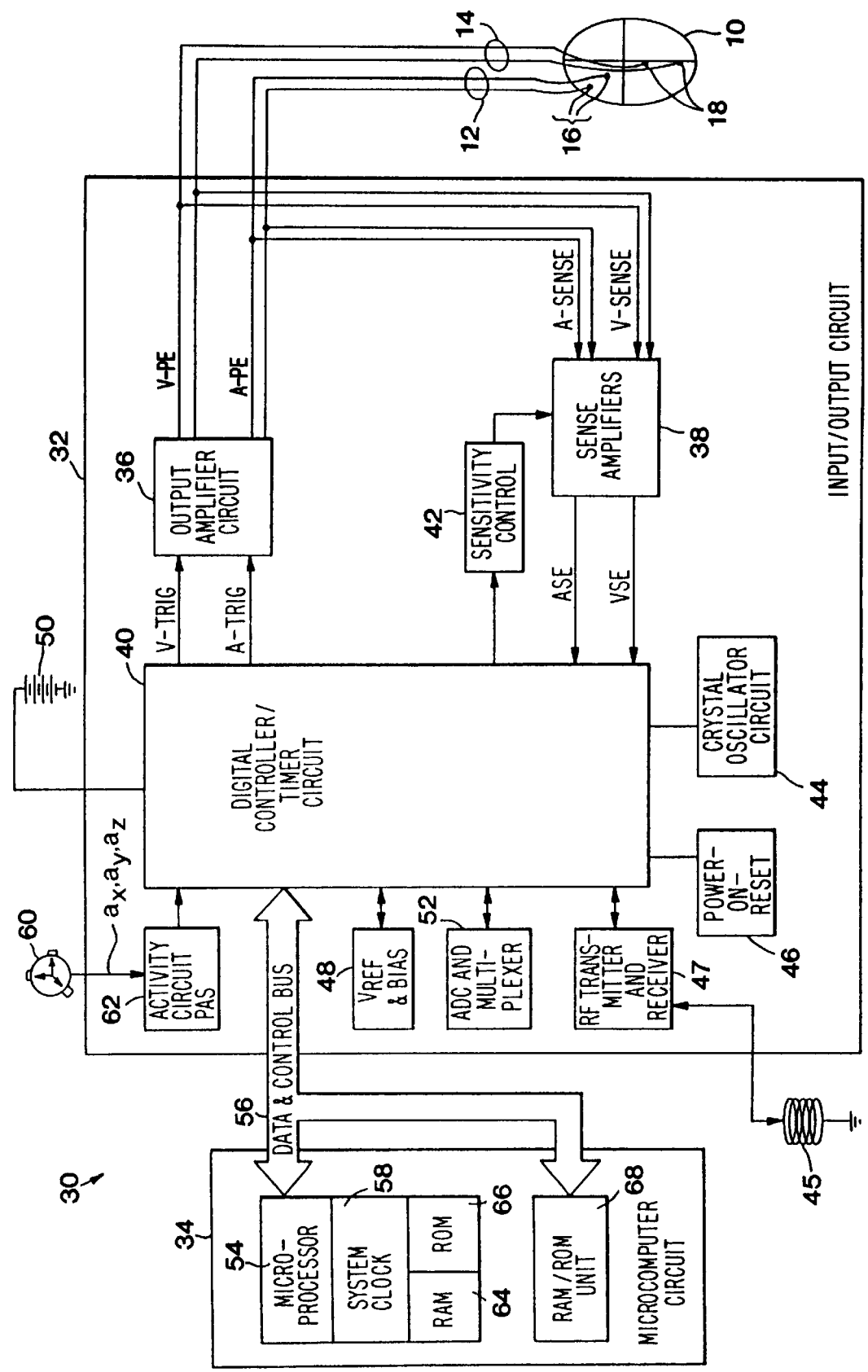
FIG. 1 is block level diagram of an exemplary IMD, namely a DDDR pacemaker, capable of implementing the mutually orthogonal DC accelerometers of the present invention as activity and patient posture sensors.

For purposes of illustration, the present invention will be described in the context of a multi-programmable DDDR pacemakers of types widely known in the prior art as described in the above-incorporated '431 and '562 patents. The illustrated IPG block diagram of FIG. 1 is merely exemplary of an IMD having components which can be used in the practice of the present invention. FIG. 1 corresponds to the general functional organization of most multi-programmable microprocessor controlled DDD(R) cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 66 of the microcomputer circuit 34. However, the present invention may also be usefully practiced by means of a full custom integrated circuit, for example, a circuit taking the form of a state machine in which a state counter serves to control an arithmetic logic unit to perform calculations according to a prescribed sequence of counter controlled steps.

Figure 2:
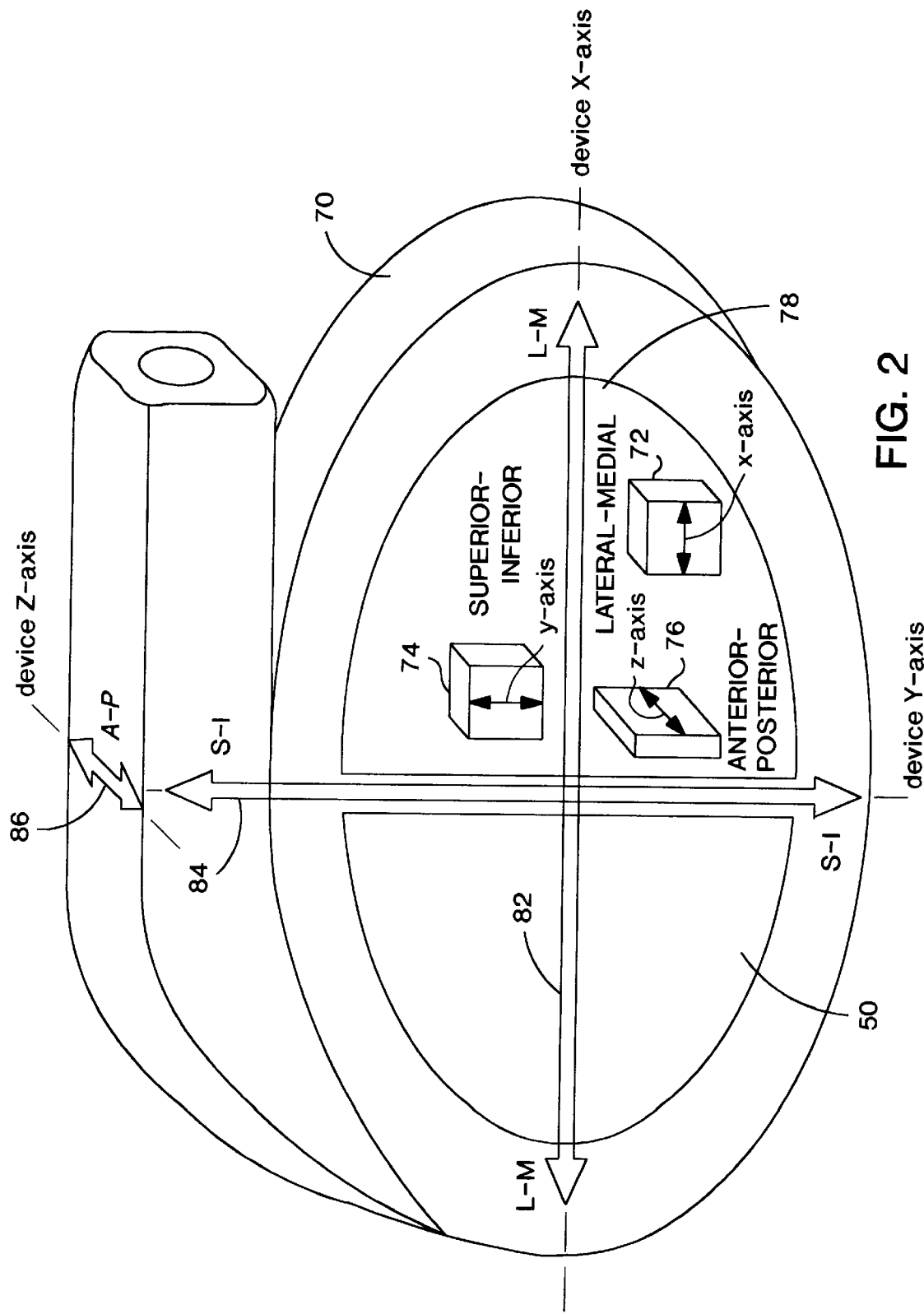
FIG. 2 is a schematic illustration of the X, Y and Z device axes of the sensitive axes of three DC accelerometers mounted orthogonally with respect to a hybrid circuit substrate within an IMD housing and correlated to S-I, L-M and A-P implantation markings on the IMD housing for orienting the IMD housing with the corresponding patient body axes and as closely as possible to the ideal X, Y and Z axes.
Figure 3:
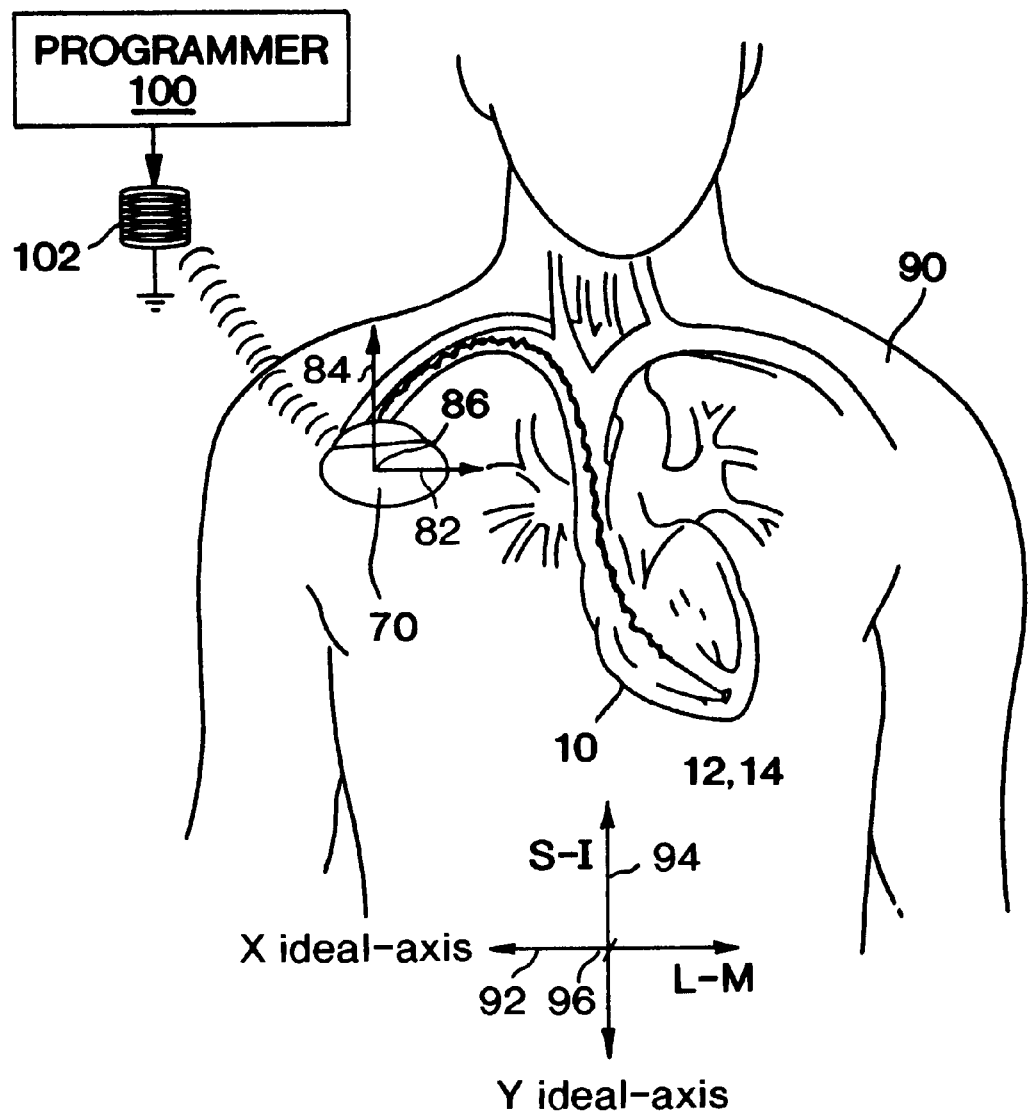
FIG. 3 is an illustration of the implantation of the IMD of FIG. 2 in a patient's body in substantial alignment with the S-I, L-M and A-P body axes and the ideal X, Y and Z axes.

FIGS. 1–3 depict such an exemplary DDDR pacemaker pulse generator in an IMD housing 70 that is intended to be implanted in a patient's body 90 with a lead or leads 12, 14 extending into the patient's heart 10. FIG. 2 is a schematic illustration of the solid state, X or L-M DC accelerometer 72, Y or S-I DC accelerometer 74, and Z or A-P DC accelerometer 76 mounted on the pulse generator hybrid circuit substrate 78 within IMD housing 70. The sensitive axes of DC accelerometers 72, 74 and 76 are orthogonally directed to one another and are aligned with the X, Y and Z device axes 82, 84, and 86. In relation to a standing patient, these X, Y and Z device axes 82, 84 and 86 correlate to S-I, L-M and A-P body axes, respectively, and the IMD housing 70 is so marked for reference. The physician can implant and stabilize the IMD in the patient's thorax region so that the X, Y and Z device axes are aligned as closely as possible to the corresponding S-I, A-P, and L-M body axes of the patient's thorax and the ideal X, Y and Z axes.

FIG. 1 is block level diagram of such a pacemaker implantable pulse generator or IPG 30 and lead set 12 and 14 which sets forth the structures required to incorporate the invention into a DDD/DDDR pacemaker. In the drawing, the patient's heart 10 has an atrial pacing lead 12 passed into the right atrium and a ventricular lead 14 passed into the right ventricle. The atrial lead 12 has an atrial electrode array 16 which couples the pulse generator 30 to the atrium. The ventricular lead 14 has a ventricular electrode array 18 for coupling the pulse generator 30 to the ventricle of the patient's heart 10. Atrial and ventricular leads 12 and 14 are depicted as bipolar leads coupled to a bipolar IPG 30, although unipolar leads could be employed with a suitable IPG.

The IPG circuit 30 of FIG. 1 is divided generally into a pacing circuit 32 coupled to a battery power supply 50, an activity sensor 60 of the type described below, a telemetry antenna 45 and a microcomputer circuit 34. The pacing circuit 32 includes the atrial and ventricular output amplifier circuit 36 and sense amplifiers 38 that are coupled to the atrial and ventricular leads 12 and 14, respectively, the digital controller/timer circuit 40 and other associated components described below. The output circuit 36 and sense amplifier circuit 38 may contain atrial and ventricular pulse generators and sense amplifiers corresponding to any of those presently employed in commercially marketed dual chamber cardiac pacemakers.

Sensed atrial depolarizations (A-SENSE) or P-waves that are confirmed by the atrial sense amplifier are communicated to the digital controller/timer circuit 40 on the ASE line. Similarly, ventricular depolarizations (V-SENSE) or R-waves that are confirmed by the ventricular sense amplifier are communicated to the digital controller/timer circuit 40 on VSE. The sensitivity control block 42 adjusts sensitivity of each sense amplifier in response to control signals provided by digital controller/timer 40 that are in turn stored in memory in microcomputer circuit 34.

In order to trigger generation of a ventricular pacing or VPE pulse, digital controller/timer circuit 40 generates a trigger signal on the V-trig line. Similarly, in order to trigger an atrial pacing or APE pulse, digital controller/timer circuit 40 generates a trigger pulse on A-trig line.

Crystal oscillator circuit 44 provides the basic timing clock for the pacing circuit 30, while battery 50 provides power. Reference mode circuit 48 generates stable voltage reference and current levels for the analog circuits within the pacing circuit 30 from the battery voltage and current. Power-on-reset circuit 46 responds to initial connection of the circuit 30 to the battery 50 for defining an initial operating condition and also resets the operating condition in response to detection of a low battery energy condition. Analog to digital converter (ADC) and multiplexor circuit 52 digitizes analog signals and voltage to provide real time telemetry of ASE and VSE cardiac signals from sense amplifiers 38, for uplink transmission via RF transmitter and receiver circuit 47. Voltage reference and bias circuit 48, ADC and multiplexor 52, power-on-reset circuit 46 and crystal oscillator circuit 44 may correspond to any of those presently used in current marketed implantable cardiac pacemakers.

Data transmission to and from an external programmer (not shown, but see 100, FIG. 3) is accomplished by means of the telemetry antenna 45 and the associated RF transmitter and receiver 47, which serves both to demodulate received downlink telemetry and to transmit uplink telemetry. Such transmissions may include particularly the orientation of the IMD as information either derived relative to ideal or in some less refined form, at a current time or pulled from memory as part of a histogram under control of the uplink program or more directly under control of the programmer. For example, circuitry for demodulating and decoding downlink telemetry may correspond to that disclosed in U.S. Pat. Nos. 4,556,063 and 4,257,423, while uplink telemetry functions may be provided according to U.S. Pat. No 4,374,382, all incorporated herein by reference. Uplink telemetry capabilities will typically include the ability to transmit stored digital information as well as real time or stored EGMs of atrial and/or ventricular electrical activity, as well as transmission of Marker Channel pulses indicating the occurrence of sensed and paced depolarizations in the atrium and ventricle.

Control of timing and other functions within the pacing circuit 30 is provided by digital controller/timer circuit 40 which includes a set of timers and associated logic circuits connected with the microcomputer 34. Microcomputer 34 controls the operational functions of digital controller/timer 40, specifying which timing intervals are employed, and controlling the duration of the various timing intervals, via data and control bus 56. Microcomputer 34 contains a microprocessor 54, associated system clock 58, and on-processor RAM and ROM chips 64 and 66, respectively. In addition, microcomputer circuit 34 includes a separate RAM/ROM chip 68 to provide additional memory capacity. Microprocessor 54 is interrupt driven, operating in a reduced power consumption mode normally, and awakened in response to defined interrupt events, which may include the A-trig, V-trig, ASE and VSE signals. The specific values of the intervals defined are controlled by the microcomputer circuit 54 by means of data and control bus 56 from programmed-in parameter values and operating modes.

If the IPG is programmed to a rate responsive mode, the patient's activity level is monitored periodically, and the sensor derived pacing escape interval is adjusted proportionally. A timed interrupt, e.g., every two seconds, may be provided in order to allow the microprocessor 54 to analyze the output of the activity circuit (PAS) 62 and update the basic V-A escape interval employed in the pacing cycle. In the DDDR mode, using the microprocessor 54 controlled by a program in memory, the V-A escape interval may be selected as the variable pacing rate establishing interval, but the A-V interval and the atrial and ventricular refractory periods may also vary with the V-A escape interval established in response to patient activity.

Preferably two separate lower rate V-A interval timer functions are provided. The first is set by the physician when the base pacing rate is selected. This V-A time interval starts from the occurrence of a VPE or VPE, and provided neither an ASE nor a VSE occurs during the V-A time interval, an APE is generated after the expiration of the V-A time interval. The duration of the second lower rate time interval is a function of the measured patient activity acquired by the activity sensor 21. Typically, the V-A time interval begins with a VSE or VPE and has a time duration reflecting patient activity. In this art, such structures are well known, and a variety of techniques can be used to implement the required timer functions.

Digital controller/timer circuit 40 starts and times out these and other intervals employed over a pacing cycle comprising a successive A-V and V-A interval in a manner well known in the art. Typically, digital controller/timer circuit 40 defines an atrial blanking interval following delivery of an atrial pacing pulse, during which atrial sensing is disabled, as well as ventricular blanking intervals following atrial and ventricular pacing pulse delivery, during which ventricular sensing is disabled. Digital controller/timer circuit 40 also defines the atrial refractory period (ARP) during which atrial sensing is disabled or the ASE is ignored for the purpose of resetting the V-A escape interval. The ARP extends from the beginning of the A-V interval following either an ASE or an A-trig and until a predetermined time following sensing of a ventricular depolarization or triggering the delivery of a VPE pulse. A post-ventricular atrial refractory period (PVARP) is also defined following delivery of a VPE pulse. The durations of the ARP, PVARP and VRP may also be selected as a programmable parameter stored in the microcomputer 34. Digital controller/timer circuit 40 also controls the pulse widths of the APE and VPE pacing pulses and the sensitivity settings of the sense amplifiers 38 by means of sensitivity control 42. Digital controller timer/logic circuit 40 also times out an upper rate limit interval (URL) set by a value programmed into memory in microcomputer circuit 34. This timer is initiated by the occurrence of a VPE or VSE, and limits the upper rate at which ventricular stimuli are delivered to the heart. The lower pacing rate is established by a programmed-in V-A or A—A interval value stored in memory in microcomputer circuit 34.

The illustrated IPG block diagram of FIG. 1 is merely exemplary, and corresponds to the general functional organization of most multi-programmable microprocessor controlled DDD(R) cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention's program control being implemented primarily by means of modifications to the software stored in the likes of ROM 66 and/or RAM 64 and associated RAM/ROM unit 68 of the microcomputer circuit 34. If the device were not a pacemaker, for example, as in an implantable hemodynamic monitor or electrocardiogram storage device as for example the Medtronic REVEAL(TM) or CHRONICLE (TM), no active therapy features (such as leads in the heartl2 and 14 to deliver stimulating pulses) would be needed to implement the invention and the data resulting from this invention would be stored for later transmission to indicate patient posture relative to other physiologic parameters the device may be tracking, like electrocardiogram or blood pressurefeatures in the two mentioned trade devices.

In accordance with one aspect of the present invention, the microcomputer also makes a determination of when the patient is walking from the output of the activity circuit (PAS) 62. The detection of walking is accomplished by an activity level that would drive the pacing rate to a programmed Activities of Daily Living (ADL) rate (i.e. a rate indicative of moderate exercise) which is sustained for more than ten seconds, for example.

Each of the DC accelerometers 72, 74, 76 depicted in FIG. 2 is preferably a surface micro-machined integrated circuit with signal conditioning, e.g. the Model ADXL 50 accelerometer sold by Analog Devices, Inc., Norwood Mass. and described in detail in the article "Airbags Boom When IC Accelerometer Sees 50G", in the Aug. 8, 1991, issue of *Electronic Design*, and in "Monolithic Accelerometer with Signal Conditioning", Rev. O, published by Analog Devices, Inc., both incorporated herein by reference in their entirety. Newer devices such as the ADXL05 and ADXL02, may be preferred for some embodiments, as could other models by other companies if it is more suitable for the IMD in which it will be used. (If using one of the accelerometer types discussed or mentioned in the summary section above, the ifollowing discussion will require modification to accomodate their particular types of output signals). Employing surface micro-machining, a set of movable capacitor plates are formed extending in a pattern from a shaped polysilicon proof mass suspended by tethers with respect to a further set of fixed polysilicon capacitor plates. The proof mass has a sensitive axis along which a force between 0 G and +/−50 G effects physical movement of the proof mass and a change in measured capacitance between the fixed and movable plates. The measured capacitance is transformed by the on-chip signal conditioning circuits into a low voltage signal.

The proof mass of the ADXL 50 is coplanar with the IC chip plane it is tethered to for movement back and forth in positive and negative vector directions along a single sensitive axis. The planar orientation thus provides that the proof mass sensitive axis is along the length of the proof mass. For off the shelf use, the ADXL 50 IC chip is mounted in a TO-5 can with the positive vector direction of the sensitive axis aligned to a reference tab of the can. By using the can tab, the positive or negative vector direction of the sensitive axis can be aligned with respect to some plane or angle of the system or circuit it is used in with respect to the constant vertical direction of gravitational force. The reference tabs for the three axes are schematically illustrated in activity sensor 60 of FIG. 1 and with respect to each of the DC accelerometers 72, 74 and 76 of FIG. 2. In actual custom fabrication within the pulse generator 30, the DC accelerometers would be formed or assembled on a single IC chip and the assembly could be enclosed in a single IC package mounted to hybrid substrate 78. The assembly of the hybrid substrate 78 within the pulse generator housing 70 is precisely controlled to establish the orientations depicted in FIG. 2.

The effect of instantaneous or AC changes due to body motion acceleration can be measured by the voltage signal output level changes per unit time. As indicated in the above-incorporated publications, the ADXL 50 can discriminate instantaneous acceleration levels up to 50 Gs, which is well in excess of the sensitivity required to detect patient footfalls regardless of the intensity level that a patient could muster. The output signal levels may be scaled to a lower range, e.g. 0 to ±2–5 G through adjustment of the internal ADXL 50 buffer amplifier or custom fabrication.

FIG. 3 schematically illustrates the implantation of the pulse generator or IMD housing 70 so that the X, Y and Z device axes 82, 84, 86, are aligned as closely as possible with the patient's L-M, S-I, and A-P body axes 92, 94, 96, respectively. The A-P body or ideal Z-axis axis 96 and the device Z-axis 86 extend directly into the plane of FIG. 3. An external programmer 100 of the type described above communicates with the implanted pulse generator 30 through conventional two-way RF telemetry employing the antenna 102.

The effect of 1 G of gravitational force applied directly along the sensitive axis of a stationary ADXL 50 accelerometer provides a characteristic output voltage signal having a level or amplitude that is referenced or scaled as +1 for angular computation purposes. The effect of 1 G of gravitational force applied in precisely the opposite or negative direction to the sensitive axis provides a characteristic output voltage signal amplitude that is referenced or scaled as −1. If the sensitive axis is oriented transversely to the direction of the gravitational force, a bias voltage level output signal should be present, and that voltage signal level is referenced or scaled as 0. The degree to which the sensitive axis is oriented away or tilted from the direction of the gravitational force can also be detected by the magnitude and polarity of the output voltage signal level deviating from the bias level scaled to 0 and below the output signal level values scaled to +1 and −1. The above-referenced publications provide instructions for scaling the voltage signal levels to the 0, +1 and −1 static level values. Other scales may be employed, depending on the signal polarities and ranges employed. A microprocessor interface circuit with autocalibration of offset error and drift (possibly caused by temperature variation or other things) may also be employed.

TABLE I

| Posture | $a_x$ | $a_y$ | $a_z$ |
|---|---|---|---|
| UP | 0 | +1 | 0 |
| SUPINE | 0 | 0 | +1 |
| PRONE | 0 | 0 | −1 |
| RIGHT | −1 | 0 | 0 |
| LEFT | +1 | 0 | 0 |

Table I sets forth the ideal, scaled amplitudes of the output signals, $a_x$, $a_y$, and $a_z$, respectively, of the three DC accelerometers 72, 74 and 76 incorporated into an IMD housing 70 as depicted in FIG. 2. (The units in the ideal example would be in gravity or "g") The sensitive axis of DC accelerometer 74 is aligned to earth's gravitational field when the pulse generator 30 is implanted. Thus, when standing upright and remaining still, the amplitude or level of the output signal ay of the DC accelerometer 74 should be at +1. In this orientation, the scaled amplitudes of the output signals $a_z$ and $a_x$ of the DC accelerometers 76 and 72, respectively, should approach 0.

The scaled amplitude of the output signal $a_z$ of the DC accelerometer 76 should approach +1 or −1, respectively, when the patient lies still and supine or prone on his/her back or stomach and if the IMD housing 70 is implanted with the DC accelerometer 76 positive vector pointed anteriorly as shown in FIG. 3. In these positions, the amplitudes of the output signals $a_y$ and $a_x$ of the DC accelerometers 74 and 72, respectively, should approach 0. In the same fashion, the patient lying on the right and left sides will orient the sensitive axis of the DC accelerometer 72 with earth's gravitational field to develop the scaled amplitude of either −1 or +1 of the output signal $a_x$. The amplitudes of the output signals $a_y$ and $a_z$ of the DC accelerometers 74 and 76 should approach 0. In these ideal orientations of Table I, there is no rotation of the device axes of the IMD housing 70 with respect to earth's gravitational field.

Figure 4:
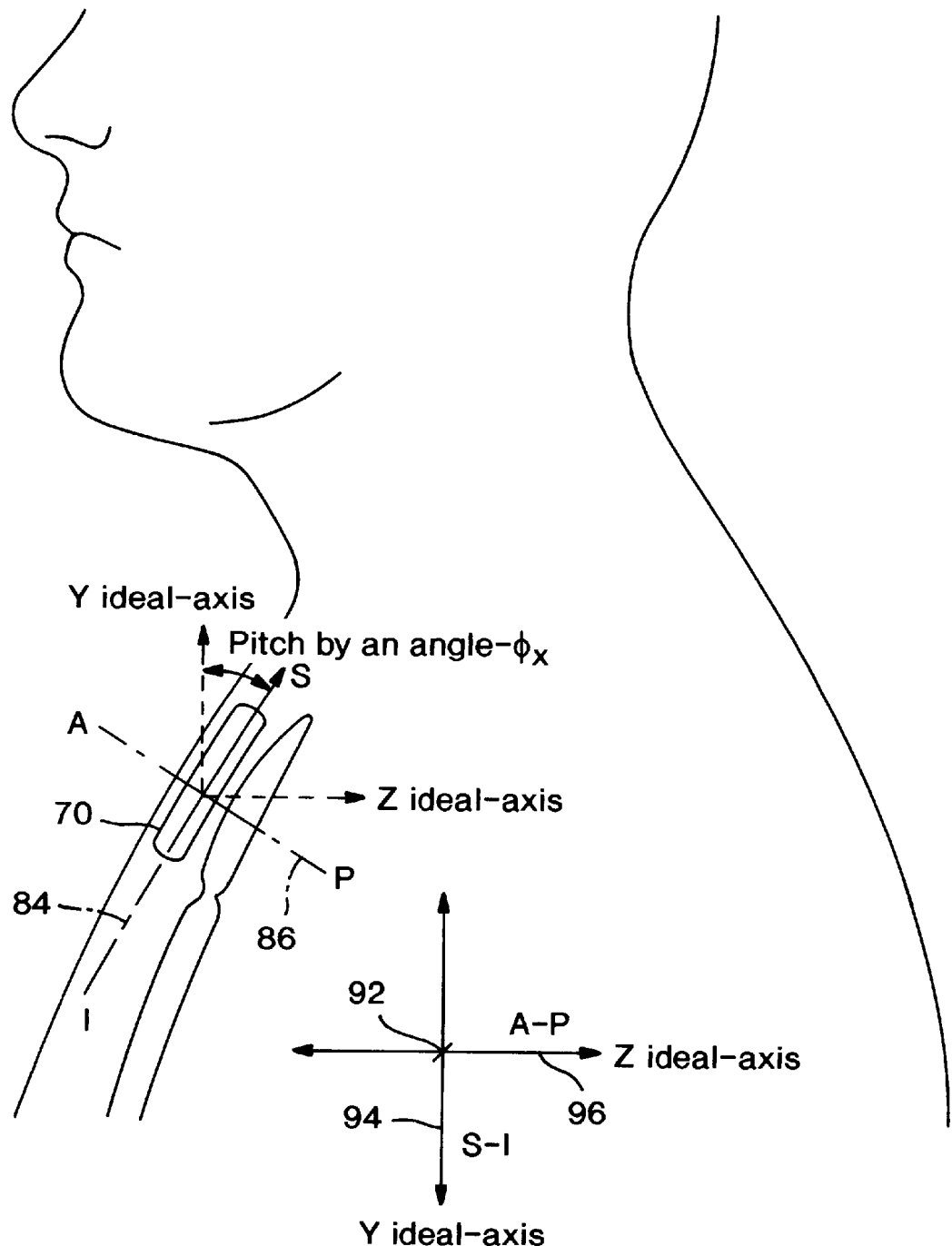
FIG. 4 illustrates the IMD housing implanted in a typical thoracic location against the patient's ribcage and rotated about the ideal X-axis at a pitch angle showing the mis-alignment of the Y and Z device axes from the ideal Y and Z axes.
Figure 5:
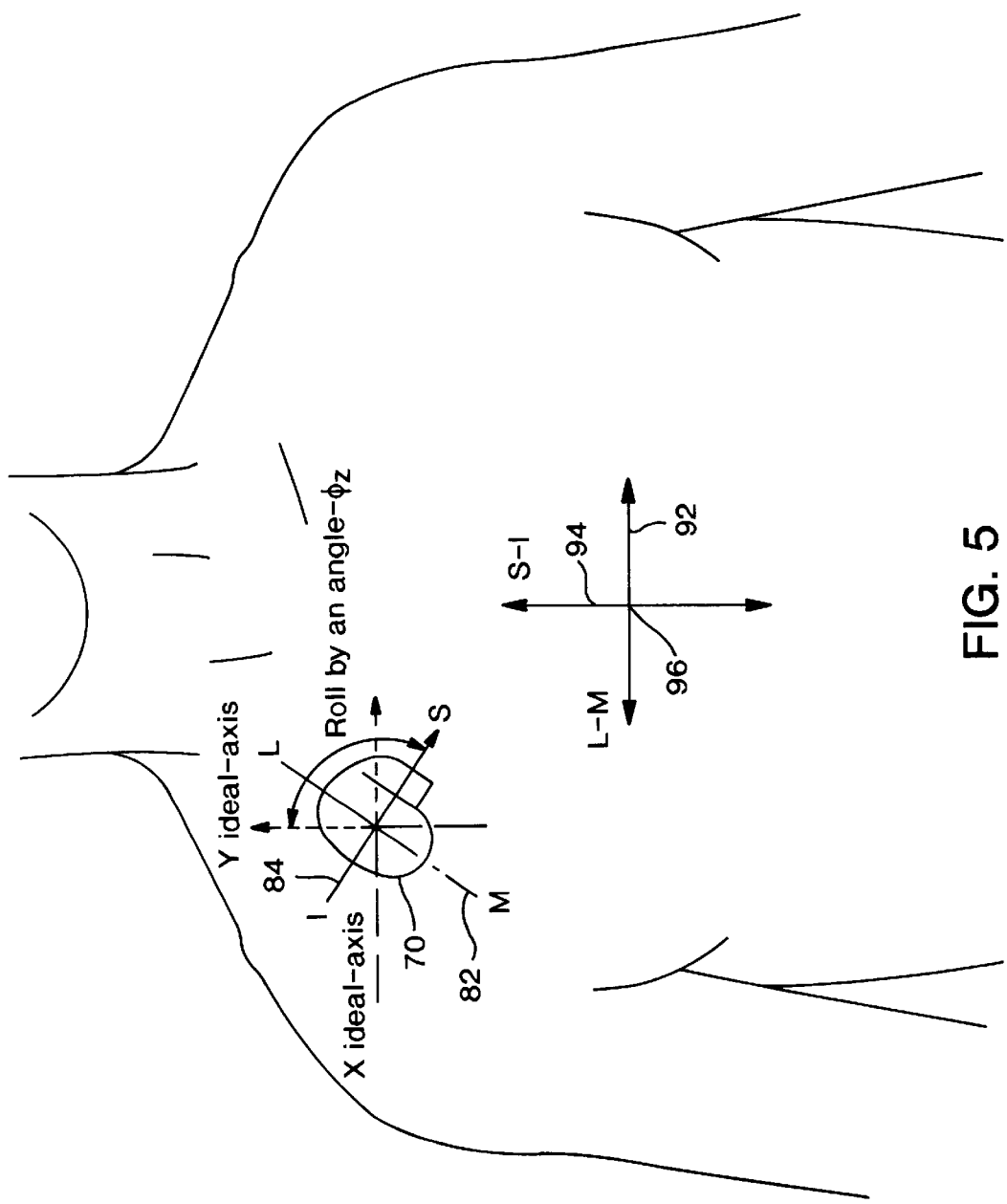
FIG. 5 illustrates the orientation of the IMD housing implanted in a typical thoracic location against the patient's ribcage and rotated about the ideal Z-axis at a roll angle showing the mis-alignment of the X and Y device axes from the ideal X and Y axes.
Figure 5A:
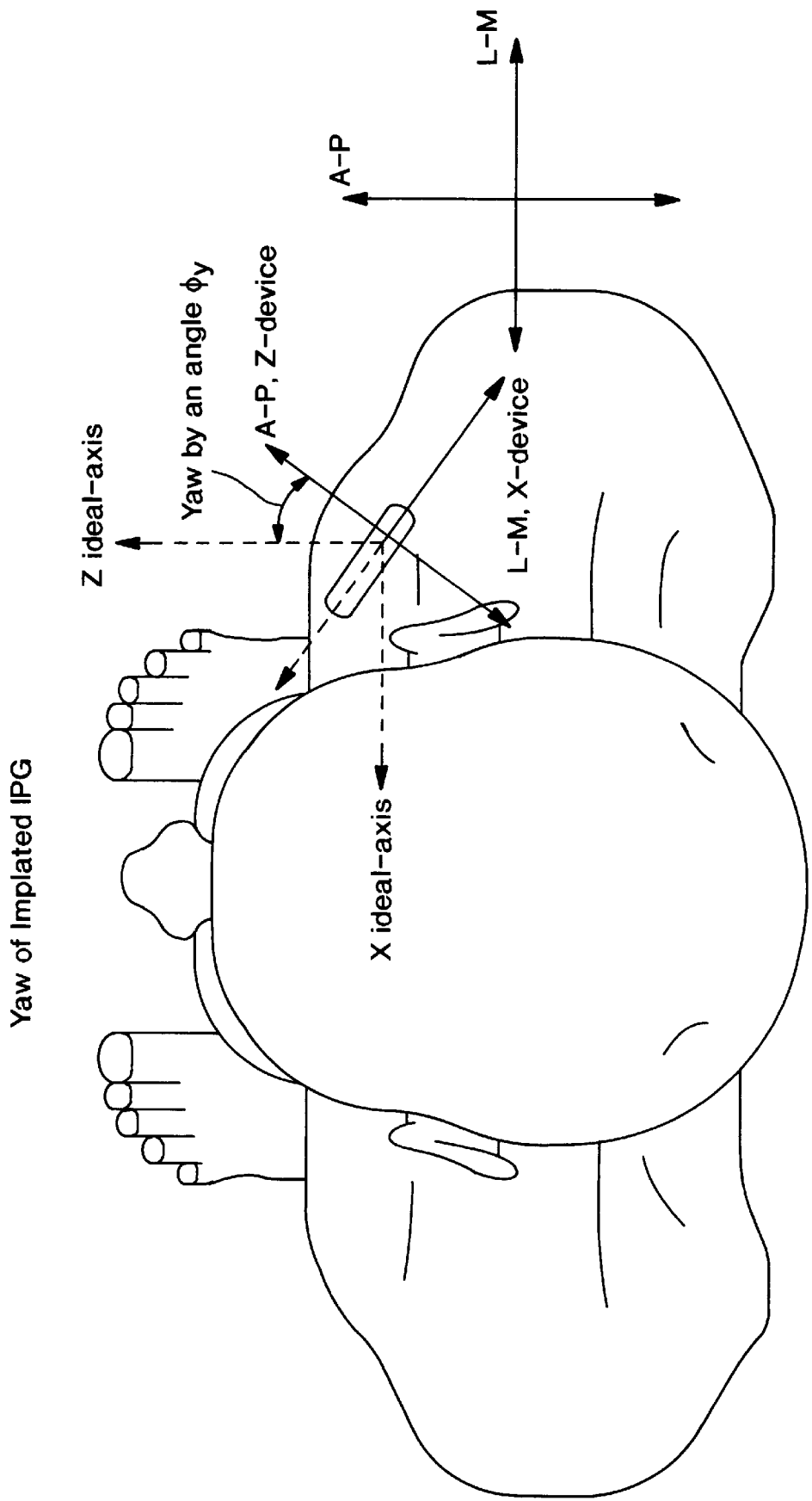
FIG. 5A illustrates the orientation of the IMD housing implanted in a thoracic location against the patient's ribcage and rotated about the ideal Y-axis at a yaw angle showing the mis-alignment of the X and Z device axes from the ideal X and Z axes.

The means and method for determining the physical posture of the patient operates through a comparison of the magnitudes and polarities of the output signals $a_x$, $a_y$, and $a_z$ with thresholds that are selected as fractions of these +/−1 and 0 levels. It is recognized that the ideal orientation of the IMD housing 70 to achieve these output signal levels is seldom achieved. FIGS. 4, 5, and 5a illustrate implantation orientations of the IMD housing 70 that do not meet the ideal orientation to the ideal X-axis ($X_{ideal}$-axis), Y-axis ($Y_{ideal}$-axis), and Z-axis ($Z_{ideal}$-axis). The angular orientations achieved at implant depend in part on the location where the IMD is implanted and sutured to the tissue under the skin in the thoracic region or lower in the abdominal region and the disposition of the attached leads or catheters, if used in the implanted system. Once implanted, the IMD typically maintains the orientation or slowly migrates or rotates either spontaneously or due to manipulation by the patient. Usually, these changes take place slowly, and so it is possible in accordance with the present invention to periodically determine the actual deviations of the device X, Y and Z axes from the ideal X, Y and Z axes and to use the deviation data to correct the DC accelerometer output signals or the thresholds that they are compared with in the determination of the patient's body posture.

In FIG. 4, the IMD housing is shown implanted in a typical thoracic location against the patient's ribcage at a pitch angle of $-\phi_x$. The pitch angle $-\phi_x$ is the angular deviation of the Y and Z device axes from the ideal Y and Z axes due to the rotation of the IMD housing 70 about the device X-axis 82. The pitch angle $\phi_x$ of rotation about the device X-axis is also shown in FIG. 6A.

FIG. 5 illustrates the rotation of the IMD housing 70 about the A-P positioning axis 86 that results in a roll angle $-\phi_z$. The roll angle $-\phi_z$ is the angular deviation of the Y and X device axes from the ideal Y and X axes due to the rotation of the IMD housing 70 about the device Z-axis 86. The roll angle $\phi_z$ of rotation about the device Z-axis is also shown in FIG. 6C.

Figure 6C:
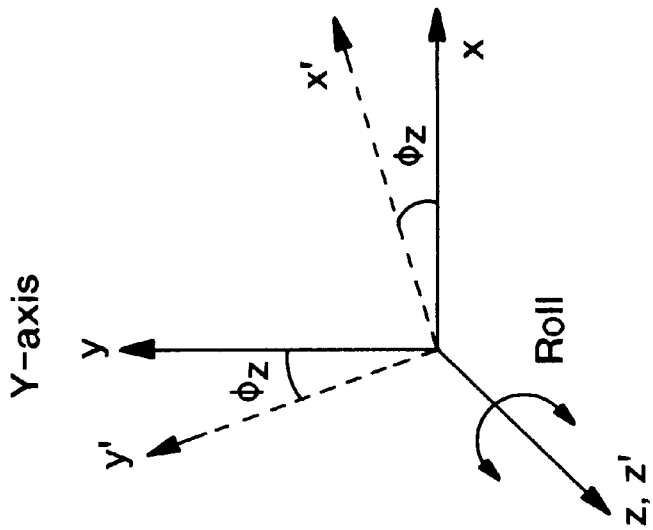
FIGS. 6A–6C illustrate pitch angle, yaw angle, and roll angles of the sensitive axes of the DC accelerometers with respect to the ideal X-axis, Y-axis and Z-axis, respectively.
Figure 6B:
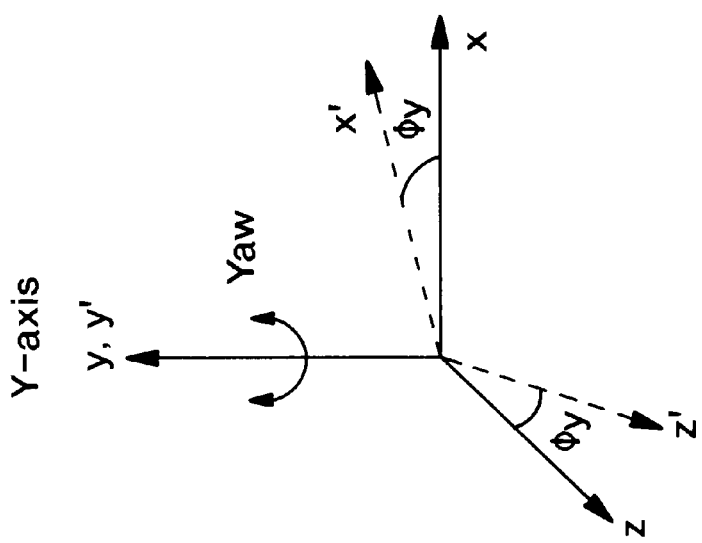
Figure 6A:
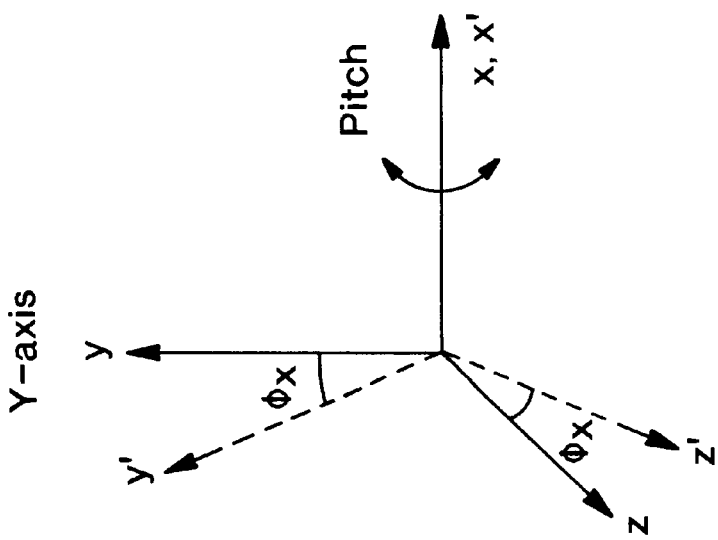

FIGS. 6A–6C illustrate the pitch angle $\phi_x$, yaw angle $\phi_y$ and roll angle $\phi_z$ deviations of the actual DC accelerometer sensitive axes that correspond to the device X-axis (denoted x'), the device Y-axis (denoted y') and the device Z-axis (denoted z') with respect to the ideal X-axis, Y-axis and Z-axis, respectively, in the standing posture of the patient. The angular deviations illustrated in FIGS. 4 and 5 frequently occur together. However, the deviation in yaw angle $\phi_y$ of the device X-axis and Z-axis does not occur very frequently, and it often is insignificant. In the autocalibration routine of the present invention, it is assumed to be insignificant enough to ignore. In the full patient work-up routine, any rotation about the device Y-axis resulting in a yaw angle $\phi_y$ of rotation illustrated in FIG. 6B is determined and taken into account. In this way, any deviations in pitch, roll and yaw from the ideal alignment of the device axes of the DC accelerometers 72, 74 and 76 with the three gravitational axes are accounted for.

Figure 7:
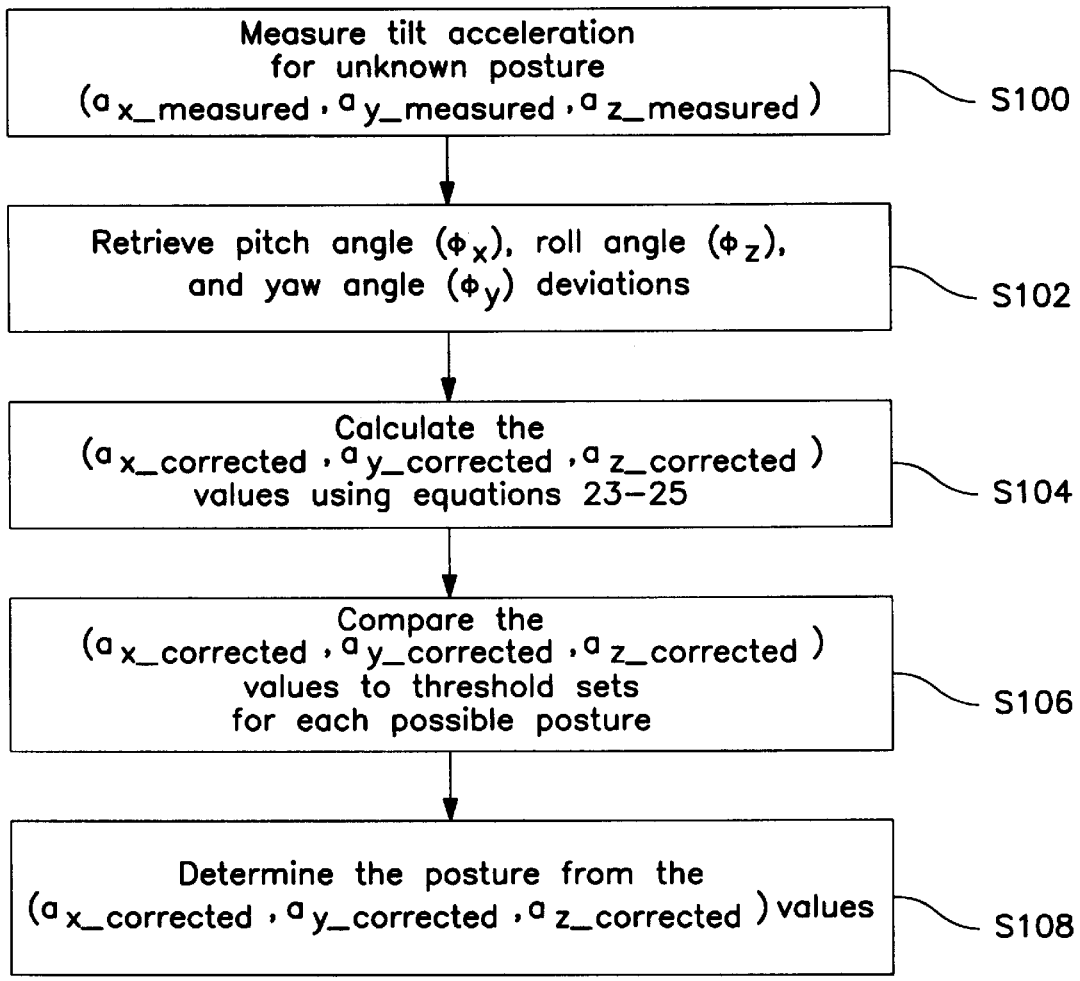
FIG. 7 is an operating algorithm for determining the patient's current posture from stored pitch, roll and yaw angles obtained in patient work-up or autocalibration modes.

FIG. 7 depicts the steps of correcting measured tilt accelerations in the normal operating mode of the IMD operating algorithm as described in the context of the DDDR pacemaker of FIG. 1 in the above-incorporated '431 patent, for example. In step S100, the measured DC accelerometer output signals $a_{x-meas}$, $a_{y-meas}$, and $a_{z-meas}$ are obtained while the patient is in the unknown posture. In step S102, the pitch angle $\phi_x$, yaw angle $\phi_y$ and roll angle $\phi_z$ deviations previously stored in RAM following the patient work-up calibration routine of FIG. 8 or the autocalibration routine of FIG. 9 are retrieved from RAM and used in step S104 to calculate the corrected DC accelerometer output signals $a_{x-corr}$, $a_{y-corr}$, and $a_{z-corr}$ using equations 23–25 described below.

Figure 8:
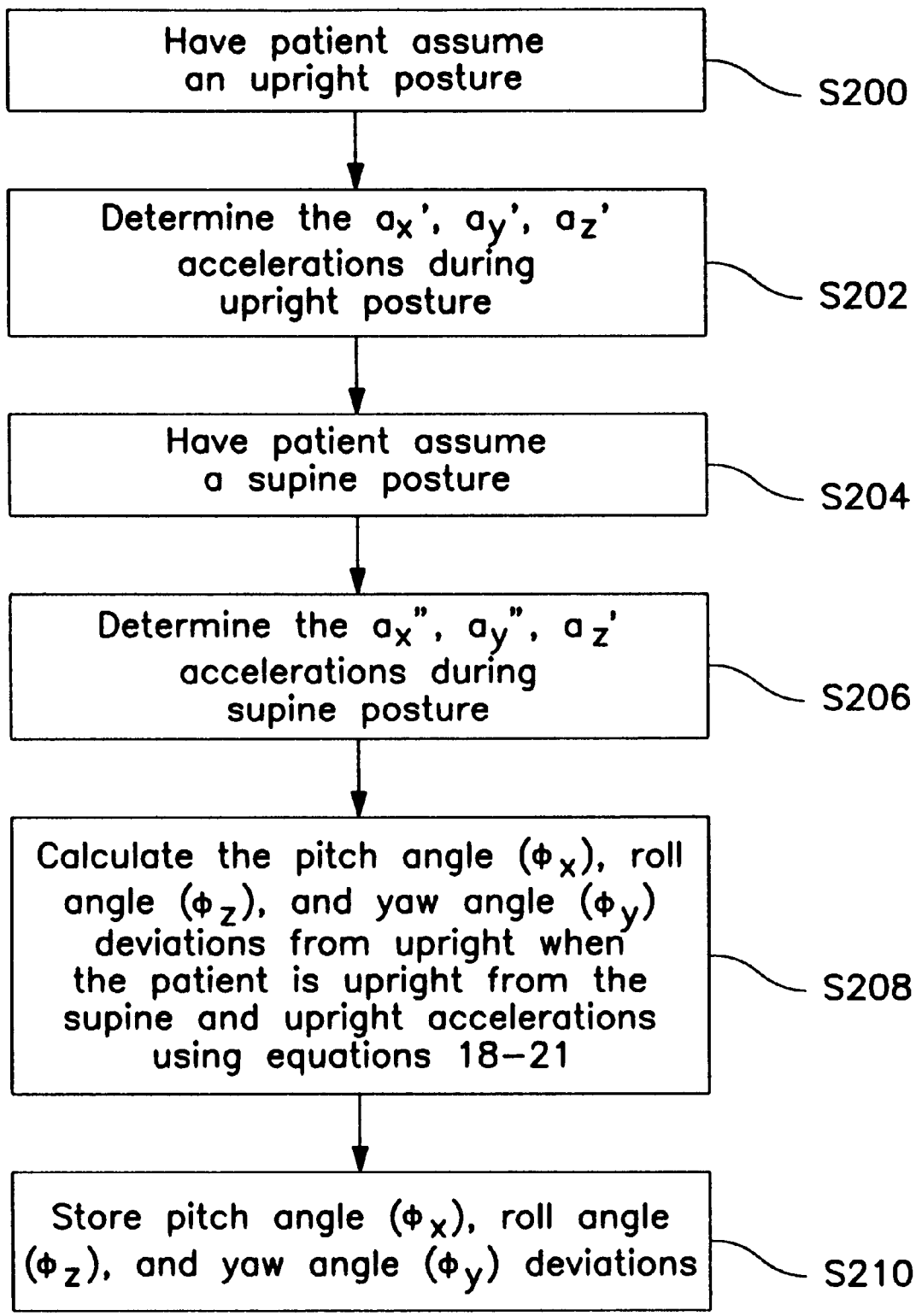
FIG. 8 is a flow chart illustrating a patient work up in two orthogonal body positions to derive the actual orientation of the sensitive axes (or device axes) of the DC accelerometers with respect to the ideal X, Y and Z axes and correction factors from any detected pitch, roll, and yaw angles for use in deriving corrected accelerometer output signals for use in determining actual patient posture.

In accordance with one aspect of the present invention illustrated in FIG. 8, the actual pitch angle $\phi_x$, yaw angle $\phi_y$ and roll angle $\phi_z$ deviations are determined in a patient work-up of steps S200–S208. The pitch angle $\phi_x$, yaw angle $\phi_y$, and roll angle $\phi_z$ deviations are stored in RAM in step S210 for use in correcting the amplitudes of the DC accelerometer output signals $a_x$, $a_y$ and $a_z$ in step S104 of FIG. 7. The patient work-up does not require the patient to assume all of the body postures or positions to store the actual DC accelerometer output signals $a_x$, $a_y$ and $a_z$ in each such position. It is only necessary for the patient to assume two orthogonal positions, e.g., the standing and supine positions or postures in steps to derive a set of standing DC accelerometer output signals $a_x'$, $a_y'$ and $a_z'$ and a set of supine DC accelerometer output signals $a_x''$, $a_y''$ and $a_z''$ in steps S202 and S206. The processing of these sets of signals in step S208 using equations 18–21 to derive the actual pitch angle $\phi_x$, yaw angle $\phi_y$ and roll angle $\phi_z$ deviations is described further below.

Figure 9:
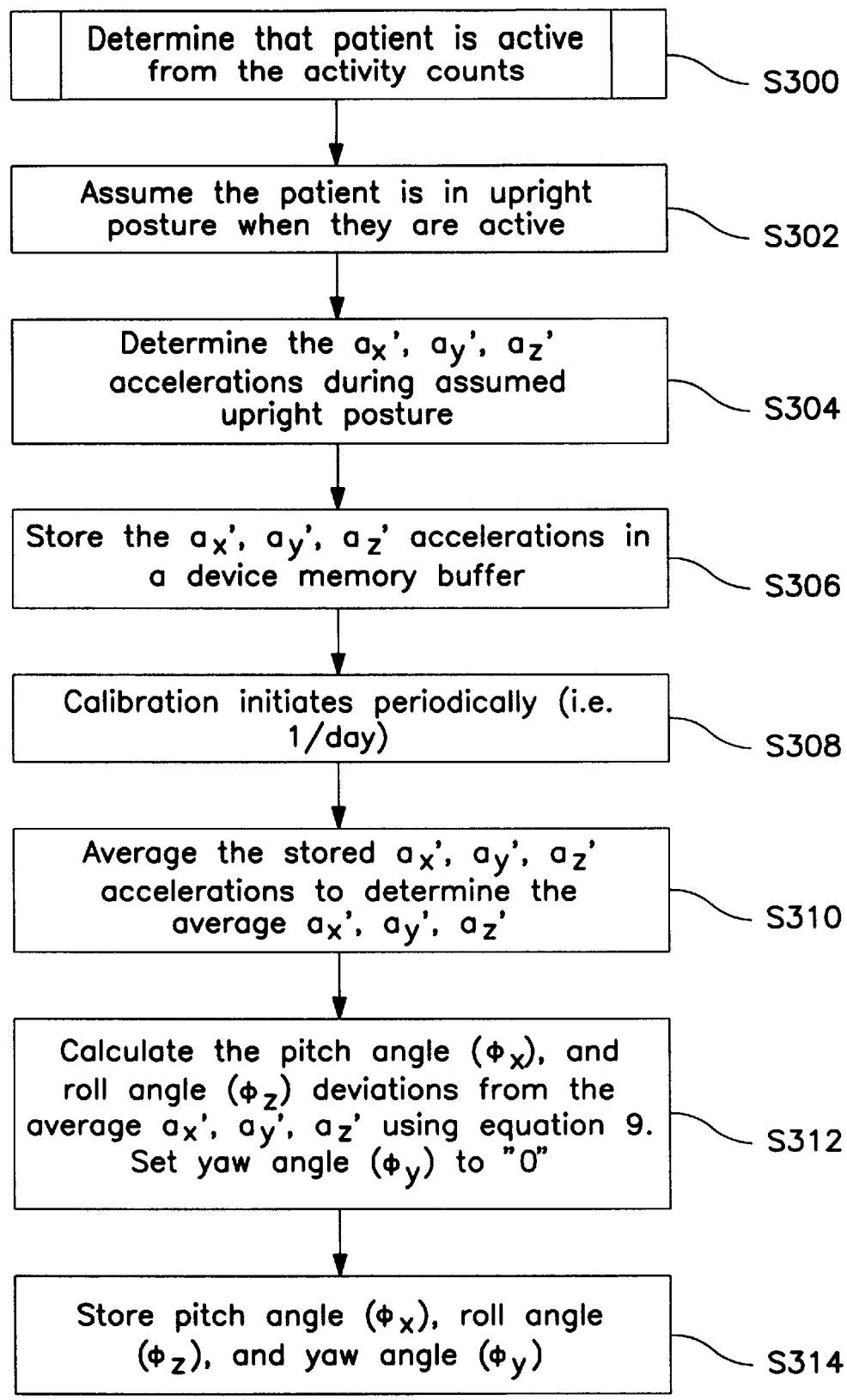
FIG. 9 is a flow chart illustrating an autocalibration routine using accelerometer signal values collected while the patient is active and assumed to be upright and assuming no significant yaw angle to derive the actual orientation of the X, Y, and Z device axes with respect to the ideal X, Y and Z axes and correction factors for use in deriving corrected accelerometer output signals for use in determining patient posture.

In a further aspect of the present invention illustrated in FIG. 9, an autocalibration mode is entered into periodically, e.g., once a day, at step S308, to derive pitch angle $\phi_x$ and roll angle $\phi_z$ from sets of DC accelerometer output signals $a_x'$, $a_y'$ and $a_z'$ that are measured in step S304 and stored in IMD memory locations in step S306 while the patient is determined to be active in steps S300–S302. In the time period between the periodic calibration, and when the activity algorithm confirms that the patient is walking at steps S302 and S304 as described above with respect to FIG. 1, the patient is assumed to be in the standing body posture. Standing body posture sets of updated DC accelerometer output signals $a_x'$, $a_y'$ and $a_z'$ are then measured in step S304 and stored in memory locations in step S306. When the internal IMD real time clock (or one could use an indication of sleep such as long inactivity or some combination to provide the trigger) determines a time of day to conduct the autocalibration in step S308, the stored sets of updated DC accelerometer output signals $a_x'$, $a_y'$ and $a_z'$ are averaged in step S310. Alternatively, the DC accelerometer output signals $a_x'$, $a_y'$ and $a_z'$ are averaged as they are derived in step S304, and the averaged DC accelerometer output signals $a_x'$, $a_y'$ and $a_z'$ are stored in step S306. As noted above, the deviation in yaw angle $\phi_y$ of the device X and Z-axes from the ideal X-and Z- axes about the ideal Y-axis does not occur very frequently, and it is assumed to be insignificant enough to set to $\phi_y=0$ in step S312. The pitch angle $\phi_x$ and roll angle $\phi_z$ deviations are derived from the averaged DC accelerometer output signals $a_x'$, $a_y'$ and $a_z'$ using equation 9 (described below) in step S310. The newly calculated pitch angle $\phi_x$ and roll angle $\phi_z$ are then stored in RAM in step S314. The stored pitch angle $\phi_x$, yaw angle $\phi_y$ and roll angle $\phi_z$ and/or correction factors of equations (23)–(25) calculated therefrom as described below are then used in correcting the amplitudes of the measured DC accelerometer output signals $a_x$, $a_y$ and $a_z$ in step S104 of FIG. 7 using the equations (23)–(25) until the next calibration takes place.

Returning to FIG. 7, the corrected DC accelerometer output signals $a_{x-corr}$, $a_{y-corr}$ and $a_{z-corr}$ are compared to a set of stored thresholds for each body posture to determine the actual body posture. The above-incorporated '431 patent describes a set of equations for deriving the patient's physical posture or position while at rest and while moving that is affected through a comparison of the magnitudes and polarities of the accelerometer output signals with these established thresholds. These thresholds and a further set of thresholds $A_x$, $A_y$, $A_z$ for a sitting position are summarized in Table II as follows:

TABLE II

| Posture | $A_x$ | $A_y$ | $A_z$ |
| --- | --- | --- | --- |
| UP | <0.2 | >0.8 | <0.2 |
| SIT | — | >0.7 | >0.2 |
| SIT | — | >0.7 | <−0.2 |
| SUPINE | — | — | >0.8 |
| PRONE | — | — | <−0.8 |
| RIGHT | >0.8 | — | — |
| LEFT | <−0.8 | — | — |

These thresholds can be programmable within the IMD and set to make the detection more or less sensitive to particular postures. In addition, it should be noted that combinations of measurements such as $A_x$ of 0.7 and $A_z$ of 0.7 would indicate a posture between supine and lying on the right side. Since these postures are both lying type postures, they can be determined to be a class of postures indicating lying down rather than indeterminate position.

The following mathematical treatment uses rotations around Cartesian coordinate device X, Y and Z axes illustrated in FIGS. 6A–6C to determine the orientation of the DC accelerometers relative to the ideal X, Y and Z axes in the standing upright position. Assume a coordinate frame shown by x, y and z axes is rotated in pitch around the x axis by an angle $\phi_x$ from the y axis towards the z axis to result in a new set of positioning axes denoted by x', y' and z' as shown in FIG. 6A. The original coordinate axes x, y and z can be expressed in terms of new coordinate axes after the rotation as:

$$x = x' \tag{1}$$

$$y = y' \cos(\phi_x) - z' \sin(\phi_x) \tag{2}$$

$$z = y' \sin(\phi_x) + \cos(\phi_x) \tag{3}$$

Similarly, rotation around the gravitational y axis by an angle $\phi_y$ from the z axis towards the x axis and rotation around z axis by an angle $\phi_z$ from the x axis towards the y axis can be calculated and placed in matrix form resulting in inverse rotation matrices $R_x^{-1}$, $R_y^{-1}$ and $R_z^{-1}$ as shown below:

$$R_x^{-1} = \begin{bmatrix} 1 & 0 & 0 \\ 0 & \cos(\phi_x) & -\sin(\phi_x) \\ 0 & \sin(\phi_x) & \cos(\phi_x) \end{bmatrix} \tag{4}$$

$$R_y^{-1} = \begin{bmatrix} \cos(\phi_y) & 0 & \sin(\phi_y) \\ 0 & 1 & 0 \\ -\sin(\phi_y) & 0 & \cos(\phi_y) \end{bmatrix}$$

$$R_z^{-1} = \begin{bmatrix} \cos(\phi_z) & -\sin(\phi_z) & 0 \\ \sin(\phi_z) & \cos(\phi_z) & 0 \\ 0 & 0 & 1 \end{bmatrix}$$

The inverse rotation matrices $R_x^{-1}$, $R_y^{-1}$ and $R_z^{-1}$ relates the new coordinate axes x', y', z' to old coordinate axes x, y, z as:

$$\begin{bmatrix} x \\ y \\ z \end{bmatrix} = R_x^{-1} \begin{bmatrix} x' \\ y' \\ z' \end{bmatrix} \begin{bmatrix} x \\ y \\ z \end{bmatrix} = R_y^{-1} \begin{bmatrix} x' \\ y' \\ z' \end{bmatrix} \begin{bmatrix} x \\ y \\ z \end{bmatrix} = R_z^{-1} \begin{bmatrix} x' \\ y' \\ z' \end{bmatrix} \tag{5}$$

Similarly, equations (1)–(3) can be solved for x', y' and z' resulting in rotation matrices $R_x$, $R_y$ and $R_z$ which are:

$$R_x = \begin{bmatrix} 1 & 0 & 0 \\ 0 & \cos(\phi_x) & \sin(\phi_x) \\ 0 & -\sin(\phi_x) & \cos(\phi_x) \end{bmatrix} \tag{6}$$

$$R_y = \begin{bmatrix} \cos(\phi_y) & 0 & -\sin(\phi_y) \\ 0 & 1 & 0 \\ \sin(\phi_y) & 0 & \cos(\phi_y) \end{bmatrix}$$

$$R_z = \begin{bmatrix} \cos(\phi_z) & \sin(\phi_z) & 0 \\ -\sin(\phi_z) & \cos(\phi_z) & 0 \\ 0 & 0 & 1 \end{bmatrix}$$

These rotation matrices relate the old coordinate axes x, y, z to the new coordinate axes x', y' and z'.

For the case where the IMD housing 70 deviates from its ideal position due to some roll and pitch angle but no yaw angle, then the resulting DC acceleration readings $a_x'$, $a_y'$ and $a_z'$ in the upright body posture can be expressed in terms of roll and pitch rotation matrices and ideal DC acceleration readings $a_x$, $a_y$ and $a_z$ in upright body posture. Equation 7 shows the general expression:

$$\begin{bmatrix} a_x' \\ a_y' \\ a_z' \end{bmatrix} = R_x R_z \begin{bmatrix} a_x \\ a_y \\ a_z \end{bmatrix} \tag{7}$$

Since the posture is upright, $a_x$ and $a_z$ both equal 0, and $a_y$ is equal to 1 in the ideal case. Placing these accelerometer values in equation 7 and substituting in the values for $R_x$, and $R_z$ matrices from equation (6), the following set of equations are obtained for $\phi_z$ and $\phi_x$:

$$\begin{bmatrix} a_x' \\ a_y' \\ a_z' \end{bmatrix} = \begin{bmatrix} \sin(\phi_z) \\ \cos(\phi_x)\cos(\phi_z) \\ -\sin(\phi_x)\cos(\phi_z) \end{bmatrix} \tag{8}$$

Solving the above equations (8) for the pitch angle $\phi_z$ and the roll angle $\phi_x$ yields;

$$\phi_z = \arcsin(a_x') \tag{9}$$

$$\phi_x = \arccos(a_y'/\cos(\phi_z))$$

Equation (9) will result in four pairs of solutions which can then be tested against the third equation in equation (8) that has not been used so far to reduce the solution pairs to two. Two pairs of solutions are due to the inability to determine any yaw angle (rotation around Y-axis) since the gravitational vector (Y-axis) is perpendicular to the plane of rotation. For example when $a_x'=0$, $a_y'=1$ and $a_z'=0$, there is no roll and pitch angle, i.e., $\phi_z=0°$ and $\phi_x=0°$. However, in the case where $\phi_z=180°$ and $\phi_x=180°$ the same acceleration readings will occur although the device X-axis and Z-axis end up in different locations in space. Therefore, some assumptions are necessary to pick one of the two solution pairs. A simple solution could be selecting the angles that result in a minimum of sum of absolute value of roll and pitch angles meaning that the smallest roll and pitch is more likely to occur.

An alternate method to the simple minimum sum of angles would be to utilize the polarity or sign of the Z axis accelerometer signal. This method will choose the pitch and roll angle solution, by choosing the pitch angle that is negative as the best solution. A brief explanation of the benefits of this method are presented. The anatomy of the upper pectoral region is concave and therefore the Z device axis will be tilted up as depicted in FIG. 4 and not perfectly normal to the earth's gravitational field. Therefore, the sign of the Z measurement will be positive and the pitch angle, $\phi_x$, will be negative. However if one assumes the graphics side of the IMD is facing the skin of the patient in FIG. 4, then the case where the IMD is rotated so that the graphics side of the IMD is facing the interior of the body should be examined. In this case, since the device is rotated and the anatomy of the upper pectoral region is concave, the Z device axis will be tilted down. Therefore, the sign of the Z measurement will be negative, but the correct $\phi_x$ will still be negative.

The example below illustrates this solution: Consider the case where the graphics side is facing the skin and the upper pectoral tilt is 15 degrees and there is no roll of the device as nearly depicted in FIG. 4. For this case the Y accelerometer will measure 0.966 g and the Z accelerometer will measure 0.259 g. The two solutions for the pitch and roll are: [$\phi_x=-15$, $\phi_z=0$] or [$\phi_x=165$, $\phi_z=-180$]. The proper solution is [$\phi_x=-15$, $\phi_z=0$] and both the minimum sum of the angles and the negative $\phi_x$ solution determinations are correct. Next, consider the 2nd case where the graphics side facing the interior of the body (therefore rotated 180 degrees) and the upper pectoral tilt is 15 degrees. For this case the Y accelerometer will measure 0.966 g and the Z accelerometer will measure −0.259 g. The two solutions for the pitch and roll are: [$\phi_x$=15, $\phi_z$=0] or [$\phi_x$=−165, $\phi_z$=−180]. The correct solution is [$\phi_x$=−165, $\phi_z$=−180]. The negative $\phi_x$ would have determined the correct solution, while the minimum absolute sum of the angles would have determined the incorrect solution.

However, the negative pitch angle is not always the correct determination. The determination is not correct when the Y accelerometer measurement is negative. In this case, the pitch angle should always be positive. Therefore for the examples above if the Y accelerometer is measuring negative values, so the measurements are −0.966 g for the Y accelerometer and 0.259 g for the Z accelerometer, the correct solution is [x=15, z=−180] and for the case where Y accelerometer measures −0.966 g and the Z accelerometer measures −0.259 g, the correct solution is [x=−165, z=−180].

The table below shows the correct determination of the pitch angle polarity based on the Y and Z accelerometer polarity. Once the solution with the correct pitch angle polarity is chosen, the corresponding roll angle of the solution is also correct. Likewise, the magnitudes of the pitch and roll angle solutions will be correct.

| ay | az | x |
|----|----|---|
| +  | +  | − |
| +  | −  | − |
| −  | +  | + |
| −  | −  | + |

The negative pitch angle solution determination assumes a pectoral implant site. For abdominal implants the minimum absolute sum of the angles or performing the full patient work-up would be preferred.

The next step will be the utilization of pitch and roll angles to determine the correct posture of the patient for any arbitrary posture using the information given in Table II. This is performed by multiplying the acceleration measurement vector with inverse pitch matrix $R_x^{-1}$ and inverse roll matrix $R_z^{-1}$ to obtain corrected acceleration vector that can be compared against the ranges presented in Table II. This operation can be expressed as:

$$\begin{bmatrix} a_x \\ a_y \\ a_z \end{bmatrix}_{corrected} = R_z^{-1} R_x^{-1} \begin{bmatrix} a_x \\ a_y \\ a_z \end{bmatrix}_{measured} \quad (10)$$

Substituting in the matrices for equation (4) into equation (10) yields the following corrected acceleration equations:

$$a_{x\_corr} = \cos(\phi_z)a_{x\_meas} - \cos(\phi_x)\sin(\phi_z)a_{y\_meas} + \sin(\phi_x)\sin(\phi_z)a_{z\_meas} \quad (11)$$

$$a_{y\_corr} = \sin(\phi_z)a_{x\_meas} + \cos(\phi_x)\cos(\phi_z)a_{y\_meas} - \sin(\phi_x)\cos(\phi_z)a_{z\_meas} \quad (12)$$

$$a_{z\_corr} = \sin(\phi_x)a_{y\_meas} + \cos(\phi_x)a_{z\_meas} \quad (13)$$

(Of course, in an IMD it would be preferred to use and store the correction factors to simplify the computations and make the processing more efficient. For example, for equation (11), $\cos(\phi_z)$ could be stored during calibration as correction factor A, $\cos(\phi_x)\sin(\phi_z)$ as correction factor B and so forth. This technique is useful for equations (11)–(13) and (25)–(27), where the IMD would be recalculating these often, as in for each posture determination).

If there is a yaw angle, the posture determined using the method described above could be incorrect. However, if the yaw angle is reasonably small, these simpler equations may be used for automatically correcting for the orientation.

A more accurate method of calibration that takes yaw angle into account involves using two sets of DC accelerometer output signals as noted above. The two orthogonal body postures are preferably the upright posture and the prone or supine body posture. The DC accelerometer output signals derived in the upright posture are denoted as $a_x'$, $a_y'$ and $a_z'$ whereas the DC accelerometer output signals derived in the supine posture are denoted as $a_x''$, $a_y''$ and $a_z''$. If it is assumed that IMD housing 70 is moved away from its ideal position in alignment with the gravitational X-axis, Y-axis and Z-axis due to a combination of roll, pitch and yaw by angles $\phi_z$, $\phi_x$ and $\phi_y$, then:

$$\begin{bmatrix} a_x' \\ a_y' \\ a_z' \end{bmatrix} = R_y^{-1} R_x^{-1} R_z^{-1} \begin{bmatrix} 0 \\ 1 \\ 0 \end{bmatrix} \quad (14)$$

$$\begin{bmatrix} a_x'' \\ a_y'' \\ a_z'' \end{bmatrix} = R_y^{-1} R_x^{-1} R_z^{-1} \begin{bmatrix} 0 \\ 0 \\ 1 \end{bmatrix} \quad (15)$$

Equation (14) is for the upright body position case, where $a_y=1$, $a_x=0$, and $a_z=0$ in the ideal case. Equation (15) is for the supine body position, $a_z=1$, $a_x=0$, and $a_y=0$. When the multiplication of three rotation matrices is carried out using equation (4), equations (14) and (15) can be expanded as:

$$\begin{bmatrix} a_x' \\ a_y' \\ a_z' \end{bmatrix} = \begin{bmatrix} \cos(\phi_y)\sin(\phi_z) + \sin(\phi_x)\sin(\phi_y)\cos(\phi_z) \\ \cos(\phi_x)\cos(\phi_z) \\ \sin(\phi_y)\sin(\phi_z) - \sin(\phi_x)\cos(\phi_y)\cos(\phi_z) \end{bmatrix} \quad (16)$$

$$\begin{bmatrix} a_x'' \\ a_y'' \\ a_z'' \end{bmatrix} = \begin{bmatrix} -\cos(\phi_x)\sin(\phi_y) \\ \sin(\phi_x) \\ \cos(\phi_x)\cos(\phi_y) \end{bmatrix} \quad (17)$$

Then, two solutions for the pitch angle, $\phi_x$ within 0 to 360° can be obtained from:

$$\phi_x = \arcsin(a_y'') \quad (18)$$

Similarly, for each $\phi_x$, a solution for $\phi_y$ can be obtained matching the solutions from two equations below:

$$\phi_y = \arcsin(-a_x''/\cos(\phi_x)) \quad (19)$$

$$\phi_y = \arccos(a_z''/\cos(\phi_x)) \quad (20)$$

Similarly, $\phi_z$ can be calculated from equation (16):

$$\phi_z = \arccos(ay'/\cos(\phi_x)) \quad (21)$$

Now, there are four triplets of solutions for $\phi_x$, $\phi_y$ and $\phi_z$ which can be reduced to a single solution by using the remaining two equations in equation (16) to test the triplets.

Once the pitch, yaw and roll angles $\phi_x$, $\phi_y$ and $\phi_z$ are calculated, subsequent measured DC accelerometer output signals $a_{x\_meas}$, $a_{y\_meas}$ and $a_{z\_meas}$ in any arbitrary posture can be corrected to $a_{x\_corr}$, $a_{y\_corr}$ and $a_{z\_corr}$ by applying inverse rotation transformation using the calibration rotation angles:

$$\begin{bmatrix} a_x \\ a_y \\ a_z \end{bmatrix}_{corr} = R_z^{-1} R_x^{-1} R_y^{-1} \begin{bmatrix} a_x \\ a_y \\ a_z \end{bmatrix}_{meas} \quad (22)$$

which can be expanded as:

$$a_{x\_corr} = a_{x\_meas}[\cos(\phi_y)\cos(\phi_z) - \cos(\phi_x)\sin(\phi_y)\sin(\phi_z)] - a_{y\_meas}\cos(\phi_x)\sin(\phi_z) + a_{z\_meas}[\sin(\phi_y)\cos(\phi_z) + \sin(\phi_x)\cos(\phi_y)\sin(\phi_z)] \quad (23)$$

$$a_{y\_corr} = a_{x\_meas}[\cos(\phi_y)\sin(\phi_z) + \sin(\phi_x)\sin(\phi_y)\cos(\phi_z)] + a_{y\_meas}\cos(\phi_x)\cos(\phi_z) + a_{z\_meas}[\sin(\phi_y)\sin(\phi_z) + \sin(\phi_x)\cos(\phi_y)\cos(\phi_z)] \quad (24)$$

$$a_{z\_corr} = -a_{x\_meas}[\cos(\phi_x)\sin(\phi_y)] - a_{y\_meas}\sin(\phi_x) + a_{z\_meas}\cos(\phi_x)\cos(\phi_y) \quad (25)$$

In each of the equations (23)–(25), the $a_{x\_meas}$, $a_{y\_meas}$, and $a_{z\_meas}$ values are multiplied by a correction factor, e.g., the correction factors $[\cos(\phi_y)\sin(\phi_z) + \sin(\phi_x)\sin(\phi_y)\cos(\phi_z)]$, $\cos(\phi_x)\cos(\phi_z)$, and $[\sin(\phi_y)\sin(\phi_z) + \sin(\phi_x)\cos(\phi_y)\cos(\phi_z)]$, respectively, of equation (24), for example. The three correction factors for each equation can be derived from the calculated pitch, yaw and roll angles $\phi_x$, $\phi_y$ and $\phi_z$.

In the IMD architecture of the exemplary DDDR pacemaker circuit of FIG. 1, the pitch, yaw and roll angles $\phi_x$, $\phi_y$ and $\phi_z$ and/or the correction factors used in equations (23)–(25) are stored in RAM 64 or RAM/ROM unit 68 to be used by the microprocessor 54 in performing equations (23)–(25) each time that the DC accelerometer output signals $a_{x\_meas}$, $a_{y\_meas}$ and $a_{z\_meas}$ are measured. Alternatively, the calculations of equations (23)–(25) can be performed using dedicated ICs in digital controller/timer circuit 40. A Matlab program that implements the algorithm with correction for roll, pitch and yaw is set forth in the Appendix.

Thus, in the two preferred calibration methods of the invention, the actual pitch and roll angles of the IMD device X, Y and Z axes from the ideal X, Y and Z axes are measured, and the yaw angle is either measured or assumed to be negligible. Then, subsequent measured DC accelerometer output signals $a_{x\_meas}$, $a_{y\_meas}$ and $a_{z\_meas}$ in any arbitrary posture are corrected to $a_{x\_corr}$, $a_{y\_corr}$ and $a_{z\_corr}$ using the correction factors and equations (23)–(25). The corrected signals $a_{x\_corr}$, $a_{y\_corr}$ and $a_{z\_corr}$ are compared to the stored set of thresholds $A_x$, $A_y$, $A_z$ shown in Table II for each posture or position following the procedure set forth in the above-incorporated '431 patent, for example.

In this DDDR pacemaker embodiment, the measurement of the DC accelerometer output signals $a_{x\_meas}$, $a_{y\_meas}$ and $a_{z\_meas}$ and the calculation of the corrected DC accelerometer output signals $a_{x\_corr}$, $a_{y\_corr}$ and $a_{z\_corr}$ is preferably triggered in the manner described in detail in the above-incorporated '431 and '562 patents.

As noted above, although the use of the two or three DC accelerometers are described above in relation to the determination of body posture for selecting a pacing rate, it will be understood that the present invention contemplates the use of the same in other therapeutic devices for delivering other therapies and in monitoring devices for storing body position alone or in relation to other monitored parameters. The present invention is also not limited to any particular pacing mode, and can function with prior art modes such as DDDR, AAIR, VVIR and DDIR. In addition, the detection of body position change from any body posture to any other body posture, such as from lying to an upright position or sitting to standing or standing to falling down to a horizontal orientation, for examples, may be used to set an appropriate transition pacing rate to treat syncopal patients susceptible to fainting.

It will be understood that the multi-axis, solid state, DC accelerometer described above and depicted in the drawings can be located in an IMD module that is physically separated from other IMD modules of a system as shown in the above-incorporated '404 patent. The IMD modules can be tethered together by cables as shown in the '404 patent or can communicate with one another in a variety of manners including the manners described in commonly assigned U.S. Pat. No. 4,987,897, or as done by any other IMD's incorporated herein by reference.

All such variations and modifications are intended to be within the scope of the invention claimed by this Letters Patent.

What is claimed is:

1. A method of determining the physical posture of a patient's body, having an ideal Y axis, aligned with the superior-inferior body axis, an ideal Z axis aligned with the anterior-posterior body axis, and an ideal X axis aligned with the lateral-medial body said axis in relation to earth's gravitational field comprising the steps of:

implanting a multi-axis, solid state sensor in the patient's body, said solid state sensor comprising X, Y, and Z accelerometers having X, Y, and Z device axes, respectively, orthogonally disposed to one another, which provide X, Y, and Z accelerometer output signals, respectively, of a magnitude and polarity dependent on the degree of alignment of the respective axis with earth's gravitational field;

in a calibration mode following implantation:
measuring a first set of accelerometer output signals from said X, Y, and Z accelerometers while the patient is in a first body posture;
measuring a second set of accelerometer output signals from said X, Y, and Z accelerometers while the patient is in a second body posture orthogonal to said first body posture;
from said first and second sets of accelerometer output signals, deriving a pitch angle of the Y and Z device axes from the Y ideal axis and the Z ideal axis, respectively, due to rotation of the Y and Z device axes about the X device axis;
from said X and Z sets of accelerometer output signals, deriving a yaw angle of the X and Z device axes from the X ideal axis and the Z ideal axis, respectively, due to rotation of the X and Z device axes about the Y device axis; and
from said X and Y sets of accelerometer output signals, deriving a roll angle of the X and Y device axes from the X ideal axis and the Y ideal axis, respectively, due to rotation of the X and Y device axes about the Z device axis; and in a normal operating mode, determining an unknown body posture of the patient by:
measuring the X, Y, and Z accelerometer output signals while the patient is in the unknown body posture;
correcting the measured X, Y, and Z accelerometer output signals employing the derived pitch, roll and yaw angles to derive corrected X, Y, and Z accelerometer output signals; and determining the body posture of the patient employing the corrected X, Y, and Z accelerometer output signals.

2. The method of claim 1, further comprising the step of:

defining a set of X, Y, and Z thresholds for body postures that the patient can assume with respect to earth's gravitational field; and wherein the body posture determining step further comprises the steps of:

comparing the magnitudes and polarities of the corrected X, Y, and Z accelerometer output signals with the X, Y, and Z respective thresholds of each set of thresholds; and determining the body posture of the patient most closely corresponding to the set of thresholds that is met by the X, Y, and Z corrected accelerometer output signals.

3. The method of claim 2, wherein the defining step further comprises the step of defining the sets of thresholds in relation to characteristic magnitudes and polarities of the accelerometer output signals on alignment of the device axes of the X, Y, and Z accelerometers with or normal to earth's gravitational field in each body posture.

4. The method of claim 2, wherein the defining step further comprises the step of defining the sets of thresholds in relation to characteristic magnitudes and polarities of the accelerometer output signals on alignment of the device axes of the X, Y, and Z accelerometers with or normal to earth's gravitational field in each body posture, including the upright body posture while standing or walking or running, a sitting body posture, a supine body posture, a prone body posture and left and right side lying body postures.

5. The method of any of the claims 1–4, further comprising the step of storing said determined body posture of the patient.

6. The method of any of the claims 1–4, further comprising the step of delivering a treatment therapy to the patient having a treatment parameter dependent on the determined body posture.

7. The method of any of the claims 1–4, further comprising the steps of:

storing said determined body posture of the patient; and delivering a treatment therapy to the patient having a treatment parameter dependent on the determined body posture.

8. The method of any of the claims 1–4, further comprising the steps of:

defining a characteristic activity magnitude of at least one of the first, second and third accelerometer output signals effected by body movement occurring within a predetermined frequency range signifying a threshold patient activity level; and deriving an activity level signal from said at least one of the X, Y or Z accelerometer signals exceeding said characteristic activity magnitude over a predetermined time period.

9. The method of any of the claims 1–4, further comprising the steps of:

defining a characteristic activity magnitude of at least one of the X, Y, and Z accelerometer output signals effected by body movement occurring within a predetermined frequency range signifying a threshold patient activity level;

deriving an activity level signal from said at least one of the X, Y, or Z accelerometer signals exceeding said characteristic activity magnitude over a predetermined time period; and delivering a treatment therapy to the patient having a treatment parameter dependent on the determined body posture and the activity level signal of the patient.

10. The method of any of the claims 1–4, further comprising the steps of:

defining a characteristic activity magnitude of at least one of the X, Y and Z accelerometer output signals effected by body movement occurring within a predetermined frequency range signifying a threshold patient activity level;

deriving an activity level signal from said at least one of the X, Y or Z accelerometer signals exceeding said characteristic activity magnitude over a predetermined time period; and storing said determined body posture and activity level of the patient.

11. The method of any of the claims 1–4 wherein the device's ideal axes are nominally defined as having orthogonal axes comprising a ideal Y-axis aligned with the superior-inferior body axis and aligned with earth's gravitational field, so as to measure 1 g of acceleration when the patient is in an upright body posture, a ideal X-axis normal to the ideal Y-axis aligned with the lateral-medial body axis and orthogonal to the earth's gravitational field, so as to measure 0 g of acceleration when the patient is in an upright body posture, and an ideal Z-axis normal to the ideal X-axis and the ideal Y-axis and aligned to the anterior-posterior body axis and orthogonal to the earth's gravitational field, so as to measure 0 g of acceleration when the patient is in an upright body posture, and wherein:

said implanting step further comprises implanting said multi-axis, solid state sensor in the patient's body so that the X device axis is nominally aligned with the lateral-medial body axis, the Y device axis is nominally aligned with the superior-inferior body axis, and the Z device axis is nominally aligned with the anterior-posterior body axis;

said step of measuring a first set of accelerometer output signals from said X, Y, and Z, and accelerometers is performed while the patient is in a first body posture wherein the ideal Y axis is nominally in alignment with the earth's gravitational field and ideal X and Z axes are nominally normal to the ideal Y-axis; and said step of measuring a second set of accelerometer output signals from said X, Y, and Z accelerometers is performed while the patient is in a second body posture orthogonal to said first body posture wherein one of the X or Z ideal axes is nominally in alignment with the earth's gravitational field and the other of the X or Z ideal axes and the Y ideal axis are nominally normal to the earth's gravitational field.

12. The method of any of the preceding claims 1–4, wherein the first body posture is the upright standing body posture and the second body posture is a selected one of the supine body posture, prone body posture, left side lying body posture, and right side lying body posture.

13. A method of determining the physical posture of a patient's body, having a superior-inferior body axis or ideal Y axis, an anterior-posterior body axis or ideal Z axis and a lateral-medial body axis or ideal X axis, in relation to earth's gravitational field comprising the steps of:

implanting a multi-axis, solid state sensor in the patient's body, said solid state sensor comprising X, Y and Z DC accelerometers having X, Y and Z device axes, respectively, orthogonally disposed to one another, which provide X, Y and Z DC accelerometer output signals, respectively, of a magnitude and polarity dependent on the degree of alignment of the respective device axis with earth's gravitational field;

in a calibration mode following implantation:

determining that the patient is in an upright body posture wherein said ideal Y axis is nominally into alignment with earth's gravitational field and X and Z ideal axes are nominally normal to earth's gravitational field;

setting a yaw angle of the X and Z device axes from the ideal X or lateral-medial body axis and the ideal Z or anterior-posterior body axis, respectively, at a fixed value based on the assumption of minimal rotation of the X and Z device axes about the Y device axes after implantation;

measuring at least one set of DC accelerometer output signals from the X, Y, and Z DC accelerometers in the assumed upright body posture;

deriving a pitch angle of the Y and Z device axes from the ideal Y axis and the ideal Z axis, respectively, due to rotation of the Y and Z device axes a about the X device axis from the measured set of DC accelerometer output signals; and deriving a roll angle of the X and Y device axes from the ideal X axis and the ideal Y axis, respectively, due to rotation of the X and Y device axes about the device Z axis from the measured set of DC accelerometer output signals; and in a normal operating mode, determining an unknown posture of the patient by:

measuring the X, Y, and Z DC accelerometer output signals;

correcting the measured X, Y, and Z DC accelerometer output signals employing the stored pitch, roll and yaw angles to derive corrected X, Y, and Z DC accelerometer output signals; and determining the body posture of the patient employing the corrected X, Y, and Z DC accelerometer output signals.

14. The method of claim 13, further comprising the step of:

defining a set of X, Y, and Z thresholds for each body posture that the patient can assume with respect to the orthogonal ideal axes; and wherein the body posture determining step further comprises the steps of:

comparing the magnitudes and polarities of the corrected X, Y, and Z DC accelerometer output signals with the X, Y, and Z respective thresholds of each set of thresholds; and determining the body posture of the patient corresponding to the set of thresholds that is met by the X, Y, and Z corrected DC accelerometer output signals.

15. The method of claim 14, wherein the defining step further comprises the step of defining the sets of thresholds in relation to characteristic magnitudes and polarities of the DC accelerometer output signals on alignment of the X, Y, and Z DC accelerometers with or normal to earth's gravitational field in each body posture.

16. The method of claim 14, wherein the defining step further comprises the step of defining the sets of thresholds in relation to characteristic magnitudes and polarities of the DC accelerometer output signals on alignment of the sensitive axes of the X, Y, and Z DC accelerometers with or normal to earth's gravitational field in each body posture, including the upright body posture while standing or walking or running, a sitting body posture, a supine body posture, a prone body posture and left and right side lying body postures.

17. The method of any of the claims 13–16, further comprising the step of storing said determined body posture of the patient.

18. The method of any of the claims 13–16, further comprising the step of delivering a treatment therapy to the patient having a treatment parameter dependent on the determined body posture.

19. The method of any of the claims 13–16, further comprising the steps of:

storing said determined body posture of the patient; and delivering a treatment therapy to the patient having a treatment parameter dependent on the determined body posture.

20. The method of any of the claims 13–16, wherein the step of determining that the patient is in an upright body posture further comprises the steps of:

defining a characteristic activity magnitude of at least one of the first, second and third DC accelerometer output signals effected by body movement occurring within a predetermined frequency range signifying a threshold patient activity level; and deriving an activity level signal from said at least one of the first, second or third DC accelerometer signals exceeding said characteristic activity magnitude over a predetermined time period that is characteristic of the patient walking in an upright body posture.

21. The method of any of the claims 13–16, wherein:

the step of determining that the patient is in an upright body posture further comprises the steps of:

defining a characteristic activity magnitude of at least one of the X, Y, and Z DC accelerometer output signals effected by body movement occurring within a predetermined frequency range signifying that the patient is walking in an upright body posture; and determining that the patient is walking when the current magnitude of at least one of the X, Y, and Z DC accelerometer output signals matches or exceeds the characteristic activity magnitude over a predetermined time period that is characteristic of the patient walking in an upright body posture; and the step of measuring at least one set of DC accelerometer output signals from the X, Y, and Z DC accelerometers in the assumed upright body posture further comprises:

measuring a plurality of sets of DC accelerometer output signals from the X, Y, and Z DC accelerometers in the assumed upright body posture; and averaging each set of measured DC accelerometer output signals from the X, Y, and Z DC accelerometers to derive an averaged set of DC accelerometer output signals.

22. The method of any of the claims 13–16, wherein:

the step of determining that the patient is in an upright body posture further comprises the steps of:

defining a characteristic activity magnitude of at least one of the X, Y, and Z DC accelerometer output signals effected by body movement occurring within a predetermined frequency range signifying that the patient is walking in an upright body posture; and determining that the patient is walking when the current magnitude of at least one of the X, Y, and Z DC accelerometer output signals matches or exceeds the characteristic activity magnitude over a predetermined time period that is characteristic of the patient walking in an upright body posture;

the step of measuring a set of DC accelerometer output signals from the X, Y, and Z DC accelerometers in the assumed upright body posture further comprises:

measuring a plurality of sets of DC accelerometer output signals from the X, Y, and Z DC accelerometers in the assumed upright body posture; and averaging each set of measured DC accelerometer output signals from the X, Y, and Z DC accelerometers to derive an averaged set of DC accelerometer output signals; and the steps of deriving pitch angle and roll angle further comprise;

periodically deriving a pitch angle of the Y and Z device axes from the Y and Z ideal axis, respectively, due to rotation of the Y and Z device axes about the X device axis from the measured and averaged set of DC accelerometer output signals; and periodically deriving a roll angle of the X and Y device axes from the X and Y ideal axes, respectively, due to rotation of the X and Y device axes about the Z device axis from the measured and averaged set of DC accelerometer output signals.

23. The method of any of the claims 13–16, further comprising the steps of:

defining a characteristic activity magnitude of at least one of the X, Y, and Z DC accelerometer output signals effected by body movement occurring within a predetermined frequency range signifying a threshold patient activity level; and deriving an activity level signal from said at least one of the X, Y and Z DC accelerometer signals exceeding said characteristic activity magnitude over a predetermined time period.

24. The method of any of the claims 13–16, further comprising the steps of:

defining a characteristic activity magnitude of at least one of the X, Y and Z DC accelerometer output signals effected by body movement occurring within a predetermined frequency range signifying a threshold patient activity level;

deriving an activity level signal from said at least one of the X, Y and Z DC accelerometer signals exceeding said characteristic activity magnitude over a predetermined time period; and delivering a treatment therapy to the patient having a treatment parameter dependent on the determined body posture and the activity level signal of the patient.

25. The method of any of the claims 13–16, further comprising the steps of:

defining a characteristic activity magnitude of at least one of the first, X, Y and Z DC accelerometer output signals effected by body movement occurring within a predetermined frequency range signifying a threshold patient activity level;

deriving an activity level signal from said at least one of the X, Y and Z DC accelerometer signals exceeding said characteristic activity magnitude over a predetermined time period; and storing said determined body posture and activity level of the patient.

26. The method of any of an claims 13–16 wherein the ideal coordinate system is nominally defined as having ideal axes comprising a ideal Y-axis aligned to earth's gravitational field, nominally aligned with the superior-inferior body axis, so as to measure 1 g of acceleration when the patient is in an upright body posture, an ideal X-axis normal to the ideal Y-axis and nominally aligned with the lateral-medial body axis, so as to measure 0 g of acceleration when the patient is in an upright body posture, and an ideal Z-axis normal to the ideal X-axis and the ideal Y-axis and nominally aligned to the anterior-posterior body axis, so as to measure 0 g of acceleration when the patient is in an upright body posture, and wherein:

said implanting step further comprises implanting said multi-axis, solid state sensor in the patient's body so that the X device axis is nominally aligned with the lateral-medial body axis, the Y device sensitive axis is nominally aligned with the superior-inferior body axis, and the Z device axis is nominally aligned with the anterior-posterior body axis; and said step of measuring a set of DC accelerometer output signals from said X, Y and Z DC accelerometers is performed while the patient is in an assumed upright body posture such that the Y device axis is nominally in alignment with the earth's gravitational field and the X and Z device axes are nominally normal to the earth's gravitational field.

27. In an implantable medical device, a system for determining the body posture of a patient's body having an ideal Y axis aligned with the superior-inferior body axis, an ideal Z axis aligned with the anterior-posterior body axis and an ideal X axis aligned with lateral-medial body axis, in relation to earth's gravitational field comprising:

a multi-axis, solid state sensor, comprising X, Y and Z DC accelerometers having X, Y and Z device axes, respectively, orthogonally disposed to one another, which provide X, Y and Z DC accelerometer output signals, respectively, of a magnitude and polarity dependent on the degree of alignment of the respective device axis with earth's gravitational field, the multi-axis, solid state sensor associated with the implantable medical device and adapted to be implanted in the patient's body so that the X device axis is nominally aligned with the lateral-medial body axis, the Y device axis is nominally aligned with the superior-inferior body axis, and the Z device axis is nominally aligned with the anterior-posterior body axis;

means for correcting for deviations in alignment of the X device axis from the ideal X axis or lateral-medial body axis, the Y device axis from the ideal Y axis or superior-inferior body axis, and the Z device axis from the ideal Z axis or anterior-posterior body axis following implantation of the medical device comprising:

means for measuring a first set of DC accelerometer output signals from said X, Y and Z DC accelerometers while the patient is in a first body posture such that the Y device axis is nominally in alignment with earth's gravitational field and the X and Z device axes are nominally normal to earth's gravitational field;

means for measuring a second set of DC accelerometer output signals from said X, Y and Z DC accelerometers while the patient is in a second body posture orthogonal to said first body posture wherein one of the X or Z device axes is generally in alignment with earth's gravitational field and the other of the X and Z device axes and the Y device axis are nominally normal to earth's gravitational field;

means for deriving a pitch angle of the Y and Z device axes from the Y and Z ideal axis respectively, due to rotation of the Y and Z device axes about the X device axis from said first and second sets of DC accelerometer output signals;

means for deriving a yaw angle of the X and Z device axes from the ideal X and Z axis, respectively, due to rotation of the X and Z device axes about the Y device axis from said first and second sets of DC accelerometer output signals; and means for deriving a roll angle of the X and Y device axes from the ideal X and Y axis, respectively, due to rotation of the X and Y device axes about the Z device axis from said first and second sets of DC accelerometer output signals; and in a normal operating mode, means operable for determining an unknown body posture of the patient comprising:

means for measuring the X, Y and Z DC accelerometer output signals while the patient is in the unknown body posture;

means for correcting the measured X, Y, and Z DC accelerometer output signals employing the derived pitch, roll and yaw angles to derive corrected X, Y and Z DC accelerometer output signals; and means for determining the body posture of the patient employing the corrected X, Y and Z DC accelerometer output signals.

28. The system of claim 27, further comprising:

means for defining a set of X, Y, and Z thresholds for each body posture that the patient can assume with respect to earth's gravitational field; and wherein the body posture determining means further comprises:

means for comparing the magnitudes and polarities of the corrected X, Y and Z DC accelerometer output signals with the X, Y and Z respective thresholds of each set of thresholds; and means for determining the body posture of the patient corresponding to the set of thresholds that is met by the X, Y and Z corrected DC accelerometer output signals.

29. The system of claim 27, wherein the defining means further comprises means for defining the sets of thresholds in relation to characteristic magnitudes and polarities of the DC accelerometer output signals on alignment of the device axes of the X, Y and Z DC accelerometers with or normal to earth's gravitational field in each body posture.

30. The system of claim 27, wherein the defining means further comprises means for defining the sets of thresholds in relation to characteristic magnitudes and polarities of the DC accelerometer output signals on alignment of the device axes of the X, Y and Z DC accelerometers with or normal to earth's gravitational field in each body posture, including the upright body posture while standing or walking or running, a sitting body posture, a supine body posture, a prone body posture and left and right side lying body postures.

31. The system of any of the claims 27–30, further comprising means for storing said determined body posture of the patient.

32. The system of any of the claims 27–30, further comprising means for delivering a treatment therapy to the patient having a treatment parameter dependent on the determined body posture.

33. The system of any of the claims 27–30, further comprising:

means for storing said determined body posture of the patient; and means for delivering a treatment therapy to the patient having a treatment parameter dependent on the determined body posture.

34. The system of any of the claims 27–30, further comprising:

means for defining a characteristic activity magnitude of at least one of the X, Y and Z DC accelerometer output signals effected by body movement occurring within a predetermined frequency range signifying a threshold patient activity level;

means for deriving an activity level signal from said at least one of the X, Y or Z DC accelerometer signals exceeding said characteristic activity magnitude over a predetermined time period; and means for delivering a treatment therapy to the patient having a treatment parameter dependent on the determined body posture and the activity level signal of the patient.

35. The system of any of the claims 27–30, further comprising:

means for defining a characteristic activity magnitude of at least one of the X, Y and Z DC accelerometer output signals effected by body movement occurring within a predetermined frequency range signifying a threshold patient activity level; and means for deriving an activity level signal from said at least one of the X, Y or Z DC accelerometer signals exceeding said characteristic activity magnitude over a predetermined time period.

36. The system of any of the claims 27–30, further comprising:

means for defining a characteristic activity magnitude of at least one of the X, Y and Z DC accelerometer output signals effected by body movement occurring within a predetermined frequency range signifying a threshold patient activity level;

means for deriving an activity level signal from said at least one of the X, Y or Z DC accelerometer signals exceeding said characteristic activity magnitude over a predetermined time period; and means for storing said determined body posture and activity level of the patient.

37. The system of any of the claims 27–30, wherein the first body posture is the upright standing body posture and the second body posture is a selected one of the supine body posture, prone body posture, left side lying body posture, and right side lying body posture.

38. The system of any of the claims 27–30 wherein the device's ideal axes are nominally defined as having orthogonal gravitational axes comprising an ideal Y-axis aligned with the superior-inferior body axis and aligned with the earth's gravitational field, so as to measure 1 g of acceleration when the patient is in an upright body posture, an ideal X-axis normal to the ideal Y-axis aligned with the lateral-medial body axis and orthogonal to the earth's gravitational field, so as to measure 0 g of acceleration when the patient is in an upright body posture, and an ideal Z-axis normal to the ideal X-axis and the ideal Y-axis and aligned to the anterior-posterior body axis and orthogonal to the earth's gravitational field, so as to measure 0 g of acceleration when the patient is in an upright body posture; and wherein the first body posture is the upright standing body posture and the second body posture is a selected one of the supine body posture, prone body posture, left side lying body posture, and right side lying body posture; wherein said first set of DC accelerometer output signals from said X, Y and Z DC accelerometers is measured while the patient is in the upright standing body posture such that the Y device axis is nominally in alignment with the earth's gravitational field and the X and Z device axes are nominally normal to the earth's gravitational field; and said second set of DC accelerometer output signals from said X, Y and Z DC accelerometers is performed while the patient is in a selected one of the supine body posture, prone body posture, left side lying body posture, and right side lying body posture wherein one of the X or Z device axes is generally in alignment with the earth's gravitational field and the other of the X or Z device axes and the Y device axis are nominally normal to the earth's gravitational field.

39. An implantable medical device employing a system of determining the body posture of a patient's body, having an ideal Y axis or superior-inferior body axis, an ideal Z axis or anterior-posterior body axis and an ideal X-axis or lateral-medial body axis, in relation to earth's gravitational field, comprising:

a multi-axis, solid state sensor, comprising X, Y and DC accelerometers having X, Y and Z device axes, respectively, orthogonally disposed to one another, which provide X, Y and Z DC accelerometer output signals, respectively, of a magnitude and polarity dependent on the degree of alignment of the respective device axis with earth's gravitational field, the multi-axis, solid state sensor associated with the implantable medical device and adapted to be implanted in the patient's body so that the X device axis is nominally aligned with the lateral-medial body axis, means operable assuming a minimal deviation of the yaw angle or the rotation of the X and Z device axis around the Y device axis at the site of implantation for correcting for deviations in alignment of the actual device axes from the ideal device axes, means for determining that the patient is in an upright body posture wherein said Y device axis is nominally aligned with earth's gravitational field and X and Z device axes are nominally normal to earth's gravitational field;

means for setting a yaw angle of the X and Z device axes from the ideal X and, respectively, at a fixed value based on the assumption of minimal rotation of the X and Z device axes around the Y device axis means for measuring at least one set of DC accelerometer output signals from the X, Y, and Z DC accelerometers while the patient is in the assumed upright body posture;

means for deriving a pitch angle of the Y and Z device axes from the ideal Y and Z device respectively, due to rotation of the Y and Z device axes about the X device axis from the measured set of DC accelerometer output signals; and means for deriving a roll angle of the X and Y device axes from the ideal X and Y axes, respectively, due to rotation of the X and Y device axes about the Z device axis from the measured set of DC accelerometer output signals; and in a normal operating mode, means for determining an unknown posture of the patient comprising:

means for measuring the X, Y and Z DC accelerometer output signals;

means for correcting the measured X, Y and Z DC accelerometer output signals employing the stored pitch, roll and yaw angles to derive corrected X, Y and Z DC accelerometer output signals; and means for determining the body posture of the patient employing the corrected X, Y and Z DC accelerometer output signals.

40. The system of claim 39, further comprising:

means for defining a set of X, Y and Z thresholds for each body posture that the patient can assume with respect to the orthogonal gravitational axes; and wherein the body posture determining means further comprises:

means for comparing the magnitudes and polarities of the corrected X, Y and Z DC accelerometer output signals with the X, Y and Z=respective thresholds of each set of thresholds; and means for determining the body posture of the patient corresponding to the set of thresholds that is met by the X, Y and Z corrected DC accelerometer output signals.

41. The system of claim 39, wherein the defining means further comprises means for defining the sets of thresholds in relation to characteristic magnitudes and polarities of the DC accelerometer output signals on alignment of the device axes of the X, Y and Z DC accelerometers with or normal to earth's gravitational field in each body posture.

42. The system of claim 39, wherein the defining means further comprises means for defining the sets of thresholds in relation to characteristic magnitudes and polarities of the DC accelerometer output signals on alignment of the device axes of the X, Y and Z DC accelerometers with or normal to earth's gravitational field in each body posture, including the upright body posture while standing or walking or running, a sitting body posture, a supine body posture, a prone body posture and left and right side lying body postures.

43. The system of any of the claims 39–42, further comprising means for storing said determined body posture of the patient.

44. The system of any of the claims 39–42, further comprising means for delivering a treatment therapy to the patient having a treatment parameter dependent on the determined body posture.

45. The system of any of the claims 39–42, further comprising:

means for storing said determined body posture of the patient; and means for delivering a treatment therapy to the patient having a treatment parameter dependent on the determined body posture.

46. The system of any of the claims 39–42, wherein means for determining that the patient is in an upright body posture further comprises:

means for defining a characteristic activity magnitude of at least one of the first, second and third DC accelerometer output signals effected by body movement occurring within a predetermined frequency range signifying a threshold patient activity level; and means for deriving an activity level signal from said at least one of the first, second or third DC accelerometer signals exceeding said characteristic activity magnitude over a predetermined time period that is characteristic of the patient walking in an upright body posture.

47. The system of any of the claims 39–42, wherein:

the means for determining that the patient is in an upright body posture further comprises:

means for defining a characteristic activity magnitude of at least one of the first, second and third DC accelerometer output signals effected by body movement occurring within a predetermined frequency range signifying that the patient is walking in an upright body posture; and means for determining that the patient is walking when the current magnitude of at least one of the X, Y and Z DC accelerometer output signals matches or exceeds the characteristic activity magnitude over a predetermined time period that is characteristic of the patient walking in an upright body posture; and the means for measuring a set of DC accelerometer output signals from the X, Y and Z DC accelerometers in the assumed upright body posture is operable for measuring a plurality of sets of DC accelerometer output signals from the X, Y and Z DC accelerometers in the assumed upright body posture, and further comprises:

means for averaging each set of measured DC accelerometer output signals from the X, Y and Z DC accelerometers to derive an averaged set of DC accelerometer output signals.

48. The system of any of the claims 39–42, wherein:

the means for determining that the patient is in an upright body posture further comprises:

means for defining a characteristic activity magnitude of at least one of the X, Y and Z DC accelerometer output signals effected by body movement occurring within a predetermined frequency range signifying that the patient is walking in an upright body posture; and means for determining that the patient is walking when the current magnitude of at least one of the X, Y and Z DC accelerometer output signals matches or exceeds the characteristic activity magnitude over a predetermined time period that is characteristic of the patient walking in an upright body posture;

the means for measuring a set of DC accelerometer output signals from the X, Y and Z DC accelerometers in the assumed upright body posture is operable for measuring a plurality of sets of DC accelerometer output signals from the X, Y and Z DC accelerometers in the assumed upright body posture, and further comprises:

means for averaging each set of measured DC accelerometer output signals from the X, Y and Z DC accelerometers to derive an averaged set of DC accelerometer output signals; and the means for deriving pitch angle and roll angle further comprise;

means for periodically deriving a pitch angle of the Y and Z device axes from the ideal Y and Z axes, respectively, due to rotation of the Y and Z device axes about the X device axis from the measured and averaged set of DC accelerometer output signals; and means for periodically deriving a roll angle of the X and Y device sensitive axes from the ideal X and Y device axes, respectively, due to rotation of the X and Y device axes about the Z device axis from the measured and averaged set of DC accelerometer output signals.

49. The system of any of the claims 39–42, further comprising:

means for defining a characteristic activity magnitude of at least one of the X, Y and Z DC accelerometer output signals effected by body movement occurring within a predetermined frequency range signifying a threshold patient activity level; and means for deriving an activity level signal from said at least one of the X, Y or Z DC accelerometer signals exceeding said characteristic activity magnitude over a predetermined time period.

50. The system of any of the claims 39–42, further comprising:

means for defining a characteristic activity magnitude of at least one of the X, Y and Z DC accelerometer output signals effected by body movement occurring within a predetermined frequency range signifying a threshold patient activity level;

means for deriving an activity level signal from said at least one of the X, Y and Z DC accelerometer signals exceeding said characteristic activity magnitude over a predetermined time period; and means for delivering a treatment therapy to the patient having a treatment parameter dependent on the determined body posture and the activity level signal of the patient.

51. The system of any of the claims 39–42, further comprising:

means for defining a characteristic activity magnitude of at least one of the X, Y and Z DC accelerometer output signals effected by body movement occurring within a predetermined frequency range signifying a threshold patient activity level;

means for deriving an activity level signal from said at least one of the X, Y or Z DC accelerometer signals exceeding said characteristic activity magnitude over a predetermined time period; and means for storing said determined body posture and activity level of the patient.

52. The system of any of the claims 39–42 wherein an ideal coordinate system is nominally defined as having ideal axes comprising an ideal Y axis aligned with the superior-inferior body axis and aligned to the earth's gravitational field, so as to measure 1 g of acceleration when the patient is in an upright body posture, an ideal X-axis normal to the ideal Y-axis and nominally aligned with the lateral-medial body axis, so as to measure 0 g of acceleration when the patient is in an upright body posture, and an ideal Z-axis normal to the ideal X-axis and the ideal Y-axis and nominally aligned to the anterior-posterior body axis, so as to measure 0 g of acceleration when the patient is in an upright body posture, and wherein:

said multi-axis, solid state sensor is adapted to be implanted in the patient's body so that the X device axis is nominally aligned with the lateral-medial body axis, the Y device axis is nominally aligned with the superior-inferior body axis, and the Z device axis is nominally aligned with the anterior-posterior body axis; and said means for measuring a set of DC accelerometer output signals from said, Y and Z DC accelerometers is operable while the patient is in an assumed upright body posture such that the Y device axis is nominally in alignment with the earth's gravitational field and the X and Z device axes are nominally normal to the earth's gravitational field.

53. A method of determining the physical posture of a patient's body, having an ideal Y axis, an Z axis, and an ideal X axis, in relation to earth's gravitational field comprising the steps of:

implanting a multi-axis, solid state sensor, comprising X, Y and Z DC accelerometers having X, Y and Z device axes, respectively, which respond to earth's gravitational field to provide X, Y and Z respective DC accelerometer signals of a magnitude and polarity dependent on the degree of alignment therewith, in the patient's body so that said X, Y and Z device axes are generally aligned with said lateral-medial, superior-inferior, and anterior-posterior body axes, respectively;

in a calibration mode wherein the patient is in at least one known or assumed body posture:

deriving a pitch angle of the Y and Z axes from the ideal Y and Z device axes respectively, due to rotation of the Y and Z device axes about the X device axis;

deriving a yaw angle of the X and Z device axes from the ideal X and Z axes, respectively, due to rotation of the X and Z device axes about the Y device axes; and deriving a roll angle of the X and Y device axes from the ideal X and Y axes, respectively, due to rotation of the X and Y device axes about the Z device axis; and in a normal operating mode:

measuring X, Y and Z measured DC accelerometer signals from said X, Y and Z DC accelerometers, respectively, in an unknown body posture that the patient assumes;

correcting the measured X, Y and Z DC accelerometer signals to compensate for derived pitch, roll and yaw angles resulting from mis-alignment of said X, Y and Z device axes with said ideal X, Y and axes, respectively; and determining the body posture of the patient from the corrected X, Y and Z DC accelerometer signals.

54. The method of claim 53, wherein said correcting step further comprises the steps of:

calculating correction factors from the derived pitch angle, roll angle and yaw angle for correction of the measured corrected X, Y and Z DC accelerometer output signals in the correcting step.

55. The method of claim 53, wherein said correcting step further comprises the steps of:

calculating correction factors from the derived pitch angle, roll angle and yaw angle for correction of the measured corrected X, Y and Z DC accelerometer output signals in the correcting step; and storing the correction factors for use in the correcting step for a time period until the next derivation of the pitch angle, roll angle and yaw angle and calculation of the correction factors.

56. The method of any of the claims 53–55, wherein the step of deriving the yaw angle comprises setting the yaw angle of the X and Z device axes from the ideal X and Z, respectively, at a fixed value based on the assumption of minimal rotation of X and Z device axes about the Y device axes.

57. The method of any of the claims 53–55, further comprising the step of:

defining a set of X, Y and Z thresholds for each body posture that the patient can assume with respect to the orthogonal gravitational axes from a first characteristic magnitude and polarity of said X, Y and Z DC accelerometer signals on alignment of the sensitive axes of said X, Y and Z DC accelerometers with earth's gravitational field, a second magnitude and polarity of said X, Y and Z DC accelerometer signals on alignment with the earth's gravitational field, and a third characteristic magnitude and polarity of said X, Y and Z DC accelerometer signals; and wherein said determining step further comprises the steps of:

comparing the magnitudes and polarities of the X, Y and Z DC accelerometer output signals with X, Y and Z respective thresholds of each set of thresholds; and determining the body posture of the patient corresponding to the set of thresholds that is met by the X, Y and Z corrected DC accelerometer output signals.

58. A method as set forth in any of claims 1–4 or 13–16 or 53–55 further comprising the step of storing posture related data over time.

59. A method as set forth in any of claims 1–4 or 13–16 or 53–55 further comprising the step of storing device orientation relative to ideal axes over time.

60. An implantable medical device having a system for determining the physical posture of a patient's body, having an ideal Y axis, an ideal Z axis and an ideal X axis, in relation to earth's gravitational field comprising:

a multi-axis, solid state sensor, comprising X, Y and Z DC accelerometers having X, Y and Z device axes, respectively, orthogonally disposed to one another, which provide X, Y and Z DC accelerometer output signals, respectively, of a magnitude and polarity dependent on the degree of alignment of the respective device axis with the earth's gravitational field, the multi-axis, solid state sensor associated with the implantable medical device and adapted to be implanted in the patient's body so that the X device axis is nominally aligned with the lateral-medial body axis, the Y device axis is nominally aligned with the superior-inferior body axis, and the Z device axis is nominally aligned with the anterior-posterior body axis;

means for correcting for deviations in alignment of the X device axis from the ideal X axis or lateral-medial body axis, the Y device axis from the ideal Y axis or superior-inferior body axis, and the Z device axis from the ideal Z axis or anterior-posterior body axis following implantation of the medical device comprising:

means operable in a calibration mode with the patient in at least one known or assumed body posture for deriving a pitch angle of the Y and Z device axes from the ideal Y and Z axes, respectively, due to rotation of the Y and Z device axes about the X device axis in the implantation step;

means operable in the calibration mode with the patient in at least one known or assumed body posture for deriving a yaw angle of the X and Z device axes from the ideal X and Z axes, respectively, due to rotation of the X and Z device axes about the Y device axis in the implantation step; and means operable in the calibration mode with the patient in at least one known or assumed body posture for deriving a roll angle of the X and Y device axes from the ideal X and Y axes, respectively, due to rotation of the X and Y axes about the Z device axis in the implantation step;

means operable in a normal operating mode when the patient assumes an unknown body posture for deriving X, Y and Z measured DC accelerometer signals from said X, Y and Z DC accelerometers, respectively;

means for correcting the measured X, Y and Z DC accelerometer signals for determined pitch, roll and yaw angular deviations resulting from mis-alignment of said X, Y and Z device axes with said ideal X, Y and Z axes, respectively; and means for determining the body posture of the patient from the corrected X, Y and Z DC accelerometer signals.

61. The system of claim 60, wherein said correcting means further comprises means for calculating correction factors from the derived pitch angle, roll angle and yaw angle for correction of the measured corrected X, Y and Z DC accelerometer output signals in the correcting step.

62. The system of claim 60, wherein said correcting means further comprises:

means for calculating correction factors from the derived pitch angle, roll angle and yaw angle for correction of the measured corrected X, Y and Z DC accelerometer output signals in the correcting step; and means for storing the correction factors for use in the correcting step for a time period until the next derivation of the pitch angle, roll angle and yaw angle and calculation of the correction factors.

63. The system of any of the claims 60-62, wherein the yaw angle deriving means further comprises means for setting the yaw angle of the X and Z device axes from the ideal X and Z axes, respectively, at a fixed value based on the assumption of minimal rotation of X and Z device axes about the Y device axis.

64. The system of any of the claims 60–62, further comprising:

a set of X, Y and Z thresholds for each body posture that the patient can assume with respect to the orthogonal gravitational axes from a first characteristic magnitude and polarity of said X, Y and Z DC accelerometer signals on alignment of the sensitive axes of said X, Y and Z DC accelerometers with earth's gravitational field, a second magnitude and polarity of said X, Y and Z DC accelerometer signals on alignment against earth's gravitational field, and a third characteristic magnitude and polarity of said X, Y and Z DC accelerometer signals; and wherein said determining means further comprises:

means for comparing the magnitudes and polarities of the corrected X, Y and Z DC accelerometer output signals with the X, Y and Z respective thresholds of each set of thresholds; and means for determining the body posture of the patient corresponding to the set of thresholds that is met by the X, Y and Z corrected DC accelerometer output signals.

65. A device as set forth in any of claims 27–30 or 39–42 or 58–62 wherein a memory means is adapted to store posture related data derived from said accelerometer signals, taken over time, and having telemetry means for transmitting said posture related data to an external device.

66. A device as set forth in any of claims 27–30 or 39–42 or 58–62 wherein a memory means is adapted to store posture related data derived from said accelerometer signals, taken over time, and having program means for determining from a detection of heart rate drop and at least partly from said position signals whether a condition of vasovagal syncope is likely to occur and to cause a stimulation circuit to deliver pacing stimulation at a support rate if said determination is positive.

67. A device as set forth in any of claims 27–30 or 39–42 or 58–62 wherein a memory means is adapted to store posture related data derived from said accelerometer signals, taken over time, and having program means for determining at least partly from said signals whether a patient is in an upright position and if not, then preventing the delivery of support pacing for vasovagal syncope.

68. A device as set forth in any of claims 27–30 or 39–42 or 58–62 wherein a memory means is adapted to store posture related data derived from said accelerometer signals, taken over time, and having program means adapted to trigger support pacing stimulation to an orthostatic hypotensive patient's heart if the patient is determined to be going to an upright posture from said posture related data.

* * * * *